(12) United States Patent
Diamond et al.

(10) Patent No.: US 7,803,559 B1
(45) Date of Patent: Sep. 28, 2010

(54) PROTEIN AGGREGATION REGULATORS

(75) Inventors: Marc I Diamond, San Francisco, CA (US); Sonia K Pollitt, San Mateo, CA (US)

(73) Assignee: The Regents of the University of CA, Oakland, CA (US)

( * ) Notice: Subject to any disclaimer, the term of this patent is extended or adjusted under 35 U.S.C. 154(b) by 708 days.

(21) Appl. No.: 10/915,203

(22) Filed: Aug. 9, 2004

Related U.S. Application Data

(60) Provisional application No. 60/493,629, filed on Aug. 8, 2003.

(51) Int. Cl.
*G01N 33/53* (2006.01)
(52) U.S. Cl. .................. 435/7.2; 436/501; 436/506; 436/518; 424/9.1
(58) Field of Classification Search .................. 435/7.2; 436/501, 506, 518; 424/9.1
See application file for complete search history.

(56) References Cited

U.S. PATENT DOCUMENTS

| 5,981,200 | A | 11/1999 | Tsien et al. |
| 6,348,322 | B1 | 2/2002 | Strittmatter |
| 6,815,575 | B1 * | 11/2004 | Kazemi-Esfarjani et al. .. 800/13 |

OTHER PUBLICATIONS

Ishizaki et al. (Molecular Pharmacology, 2000, vol. 57, pp. 976-983).*
Narumiya et al. (Methods in Enzymology, 2000, vol. 325, pp. 273-284).*
Iwamoto et al. (Journal of Hepatology, 2000, vol. 32, pp. 762-770).*
Pollitt et al. (Neuron, vol. 40, Nov. 13, 2003, pp. 685-694).*
Moore et al. (American Journal of Human Genetics, vol. 69, 2001, pp. 1385-1388).*
Chen et al. (Nature Medicine, vol. 6, No. 7, Jul. 2000, pp. 797-801).*
Weatherbee et al. (The Journal of Cell Biology, vol. 92, Jan. 1982, pp. 155-163).*
Bonelli RM, et al., "Minocycline for Huntington's Disease: an Open Label Study", Neurology. Mar. 11, 2003;60(5):883-4.
Desai et al, "Biologically Active Molecules that Reduce Polyglutamine Aggregation and Toxicity", Human Molecular Genetics, 2006, vol. 15, pp. 2114-2124.
Steffan JS, et al., "Histone Deacetylase Inhibitors Arrest Polyglutamine-Dependent Neurodegeneration in *Drosophila*", Nature. Oct. 18, 2001;413(6857):739-43.
Abel, Annette, et al (2001) Expression of expanded repeat androgen receptor produces neurologic disease in transgenic mice, Hum Mol Genet 10, 107-116.
Apostol, Barbara L. et al (2003) A cell-based assay for aggregation inhibitors as therapeutics of polyglutamine-repeat disease and validation in *Drosophila* PNAS 100:5950-5955.
Berciano, Maria T. et al (2004) Oculopharyngneal muscular dystrophy-like nuclear inclusions are present in normal magnocellular neurosecretory neurons of the hypothalamus. Hum Mol Genet 13:829-838.
Berthelier, Valerie et al., (2001). A microtiter palte assay for polyglutamine aggregate extension. Anal Biochem 295, 227-236.
Bolivar, V.J. et al. (2003) Exploratory Activity and Fear Conditioning Abnormalities Develop Early in R6/2 Huntington's Disease Transgenic Mice. Behavioral Neuroscience 117(6):1233-42.
Chen, M., et al. (2000) Minocycline inhibits caspase-1 and caspase-3 expression and delays mortality in a transgenic mouse model of Huntington disease. Nature Medicine 6:797-801.
Chevalier-Larsen, E.S., et al. (2004) Castration Restores Function and Neurofilament Alterations of Aged Symptomatic Males in a Transgenic Mouse Model of Spinal and Bulbar Muscular Atrophy. The Journal of Neuroscience 24(20):4778-86).
Davies, Stephen W., et al., (1997) Formation of Neuronal Intranuclear Inclusions Underlies the Neurological Dysfunction in Mice Transgenic for the HD Mutation. Cell 90:537-48.
De Angelis, Dino A. (1999) Why FRET over genomics? Physiologenomics vol. X:93-99.
Diamond, Marc I. et al., (2000) Regulation of expanded polyglutamine protein aggregation and nuclear localization by the glucocorticoid receptor. Proc Natl Acad Sci 97, 657-661.
Georgalis, Yannis et al., (1998) Huntingtin aggregation monitored by dynamic light scattering. Proc Natl Acad Sci 95, 6118-6121.
Gutekunst, Claire-Anne, et al. (1999) Nuclear and Neuropil Aggregates in Huntington's Disease: Relationship to Neuropathology. Journal of Neuroscience 19:2522-34.
Hirose, Masaya et al., (1998) Molecular Dissection of the Rho-associated Protein Kinase (p160ROCK)-regulated Neurite Remodeling in Neuroblastoma N1E-115 Cells. The Journal Cell Biology 141, 1625-1636.
Hockly, Emma, et al. (2003) Standardization and statistical approaches to therapeutic trials in the R6/2 mouse. Brain Research Bulletin 61:469-79.
Ishizaki, Toshimasa et al., (1997) p160$^{ROCK}$, a Rho-associated coiled-coil forming protein kinase, works downstream of Rho and induces focal adhesions. FEBS Lett 404, 118-124).
Ishizaki, Toshimasa et al., (2000) Pharmacological Properties of Y-27632, a Specific Inhibitor of Rho-Associated Kinases. Molecular Pharmacology 57, 976-983.
Katsuno, Masahisa et al. (2002) Testosterone Reduction Prevents Phenotypic Expression in a Transgenic Mouse Model of Spinal and Bulbar Muscular Atrophy. Neuron 35:843-854.
Kim, Soojin et al., (2002) Polyglutamine protein aggregates are dynamic. Nature Cell Biology 4, 826-831.
Krobitsch, Sylvia and Lindquist, Susan (2000) Aggregation of huntingtin in yeast varies with the length of the polyglutamine expansion and the expression of chaperone proteins. PNAS 97(4): 1589-94.

(Continued)

*Primary Examiner*—Lisa V Cook
(74) *Attorney, Agent, or Firm*—Fenwick & West LLP

(57) ABSTRACT

Disclosed herein is a high-throughput assay to measure intracellular polyglutamine protein aggregation using fluorescence resonance energy transfer (FRET). Three libraries of over 3000 biologically active small molecules were screened for inhibitory activity, and a lead compound was characterized in detail. Y-27632, an inhibitor of the Rho-associated kinase p160ROCK, diminished polyglutamine protein aggregation at micromolar concentrations, and reduced neurodegeneration in a *Drosophila* model of polyglutamine disease.

18 Claims, 7 Drawing Sheets

OTHER PUBLICATIONS

Mangiarini, Laura, et al., (1996) Exon 1 of the HD Gene with an Expanded CAG Repeat Is Sufficient to Cause a Progressive Neurological Phenotype in Transgenic Mice. Cell 87: 493-506.

Merry, D.E. et al., (1998) Cleavage, aggregation and toxicity of the expanded androgen receptor in spinal and bulbar muscular atrophy. Human Molecular Genetics 7(4), 693-701.

Miyazaki, Koji, et al., (2002) Rho-dependent Agonist-induced Spatio-temporal Change in Myosin Phosphorylation in Smooth Muscle Cells. The Journal of Biological Chemistry 277:725-34.

Muchowski, Paul J. (2002) Requirement of an intact microtubule cytoskeleton for aggregation and inclusion body formation by a mutant huntingtin fragment. PNAS 99(2), 727-732.

Narumiya, Shuh et al., (2000) [24] Use and Properties of ROCK-Specific Inhibitor Y-27632. Methods Enzymol 325, 273-284).

Pollitt, Sonia K. et al (2003) A Rapid Cellular FRET Assay of Polyglutamine Aggregation Identifies a Novel Inhibitor. Neuron 40:685-694.

Schaufele, Fred et al., (2003) Conformation of CCAAT/Enhancer-binding Protein α Dimers Varies with Intranuclear Location in Living Cells. J Biol Chem 278, 10578-10587.

Sekar, Rajesh Babu and Periasamy, Ammasi, (2003) Fluorescence resonance energy transfer (FRET) microscopy imaging of live cell protein localizations. J Cell Biol 160, 629-633.

Snyder, Evan Y. et al. (1992) Multipotent Neural Cell Lines Can Engraft and Participate in Development of Mouse Cerebellum. Cell 68:33-51.

Taylor, J. Paul et al., (2003) Aggresomes protect cells by enhancing the degradation of toxic polyglutamine-containing protein. Human Molecular Genetics 12(7), 749-757.

Uehata, Masayoshi, et al. (1997) Calcium sensitization of smooth muscle medicated by a Rho-associated protein kinase in hypertension. Nature 389:990-4).

Wanker, Erich E. et al., (1999) [24] Membrane Filter Assay for Detection of Amyloid-like Polyglutamine-Containing Protein Aggregates. Methods in Enzymology 309, 375-386).

Weatherman, R.V. et al., (2002) Ligand-Selective Interactions of ER Detected in Living Cells by Fluorescence Resonance Energy Transfer. Mol Endocrinol 16,487-496).

Welch, William J. and Diamond, Marc I. (2001) Glucocorticoid modulation of androgen receptor nuclear aggregation and cellular toxicity is associated with distinct forms of soluble expanded polyglutamine protein. Hum Mol Genet 10, 3063-3074.

Zhang, Ji-Hu et al., (2000) Confirmation of Primary Active Substances from High Throughput Screening of Chemical and Biological Populations: A Statistical Approach and Practical Considerations. J Comb Chem 2,258-265).

* cited by examiner

PROTEIN AGGREGATION REGULATORS

CROSS REFERENCE TO RELATED APPLICATIONS

This application claims the benefit of U.S. Provisional Application No. 60/493,629, filed Aug. 8, 2003, the entire disclosure of which is hereby incorporated by reference in its entirety for all purposes.

STATEMENT REGARDING FEDERALLY SPONSORED RESEARCH OR DEVELOPMENT

The U.S. Government has certain rights in this invention pursuant to Grant Nos. 1K08NS01976-01 and 1R21NS45350-01 awarded by the National Institutes of Health.

BACKGROUND OF THE INVENTION

1. Field of the Invention

The invention relates to methods and compositions for modulating protein aggregation, useful for treatment of protein aggregation diseases and elucidation of cellular pathways involved in protein aggregation.

2. Description of the Related Art

Protein Aggregation Diseases

Human neurodegenerative disorders such as the tauopathies (including, e.g., Alzheimer's disease), Parkinson disease, amyotrophic lateral sclerosis, and polyglutamine expansion diseases (including, e.g., Huntington's disease and spinobulbar muscular atrophy) are all characterized by misfolding and aggregation of pathogenic proteins. These phenomena appear closely linked to pathology, although it has been unclear whether they represent a step in pathogenesis or even a protective mechanism. It is clear, however, that polyglutamine misfolding and aggregation occurs in a controlled fashion: it is noted primarily in affected neurons in patients, and is subject to regulation within the cell by various pathways (Chen et al., (2003) Cell 113, 457-468; Diamond et al., (2000). Proc Natl Acad Sci 97, 657-661; Emamian et al., (2003). Neuron 38, 375-387; Humbert et al., (2002). Dev Cell 2, 831-837; Meriin et al., (2001). J Cell Biol 153, 851-864; Wyttenbach et al. (2000). Proc Natl Acad Sci 97, 2898-2903).

Polyglutamine expansion diseases derive from CAG-codon expansion in certain genes. This enlarges a tract of glutamines in the target protein that produces neurodegeneration when it exceeds a critical threshold. Spinobulbar muscular atrophy (SBMA) is a progressive motor neuron disease caused by polyglutamine expansion in the N-terminus of the androgen receptor (AR) (Kennedy et al. (1968). Neurology 18, 671-680; La Spada et al., (1991). Nature 352, 77-79). Huntington's disease (HD) is a progressive neuropsychiatric degenerative condition with an associated movement disorder, and derives from a similar expansion in a protein of unknown function, huntingtin (htt) (The Huntington's Disease Collaborative Research Group (1993)).

Currently there are no effective therapies for HD, SBMA, or any neurodegenerative disease. Thus, methods to discover therapeutic targets and/or small molecules and other compounds, e.g., peptides, nucleic acids, and the like, that modulate pathogenesis are of crucial importance.

Cellular toxicity in most protein aggregation diseases correlates with nuclear accumulation and inclusion formation of mutant protein, and, in certain cases, may derive from "toxic fragments" produced through proteolysis (DiFiglia et al., (1997). Science 277, 1990-1993; Ellerby et al., (1999). J Neurochem 72, 185-195; Hodgson et al., (1999). Neuron 23, 181-192; Li et al., (1998). Ann Neurol 44, 249-254; Merry et al., (1998). Hum Mol Genet 7, 693-701). Several lines of evidence suggest that cells form inclusions as a physiological response to pathogenic proteins. Neurons of the central nervous system form predominantly nuclear inclusions, especially in affected regions, whereas somatic tissues generally do not (DiFiglia et al., (1997). Science 277, 1990-1993; Li et al., (1998). Ann Neurol 44, 249-254; Paulson et al., (1997). Neuron 19, 333-344). Activation of stress pathways via heat shock or JNK activation increases polyglutamine protein aggregation (Cowan et al., (2003). Hum Mol Genet 12, 1377-1391; Meriin et al., (2001). J Cell Biol 153, 851-864; Wyttenbach et al. (2000). Proc Natl Acad Sci 97, 2898-2903). In response to activation of Akt kinase, one group has reported decreased htt toxicity and aggregation in cell models (Humbert et al., (2002). Dev Cell 2, 831-837), while others report increased ataxin-1 toxicity and aggregation (Chen et al., (2003). Cell 113, 457-468). Several reports indicate that cytoplasmic inclusion formation within cells is a microtubule-dependent process (Garcia-Mata et al., (1999). J Cell Biol 146, 1239-1254; Muchowski et al., (2002). Proc Natl Acad Sci 99, 727-732; Taylor et al., (2003). Hum Mol Genet 12, 749-757). It has also been demonstrated that over-expressed wild-type glucocorticoid receptor (GR) diminishes polyglutamine protein aggregation after activation by hormone agonist, whereas a mutant form (GRΔ) increases nuclear inclusion formation and polyglutamine-dependent toxicity (Diamond et al., (2000). Proc Natl Acad Sci 97, 657-661; Welch and Diamond, (2001). Hum Mol Genet 10, 3063-3074). Thus, polyglutamine protein conversion from a soluble to an aggregated form appears to be a highly regulated process within the cellular milieu, and is not driven simply by a propensity for self-association.

Current Assays

The cellular pathways and molecular mechanisms that regulate protein misfolding and aggregation in polyglutamine and other neurodegenerative diseases remain largely unknown. It would be useful to elucidate these pathways and mechanisms, so that they can be targeted to prevent disease progression.

A variety of high-throughput approaches have been applied to identify direct inhibitors of polyglutamine aggregation in vitro (Berthelier et al., (2001). Anal Biochem 295, 227-236; Georgalis et al., (1998). Proc Natl Acad Sci 95, 6118-6121; Wanker et al., (1999). Methods in Enzymology 309, 375-386). In these cases, formation of insoluble aggregates of purified peptides serves as a readout. However, these methods cannot uncover underlying mechanisms that regulate intracellular protein misfolding and aggregation.

Yeast assays to study protein aggregation have been developed that express polyglutamine domains (Krobitsch and Lindquist. (2000). PNAS 97(4): 1589-94.) However, the resulting aggregates are non-toxic, raising questions about the applicability of the yeast cells as a model for human disease, e.g., polyglutamine expansion diseases.

In cultured cells, two basic approaches have been used to detect aggregation: identification of macro-aggregates by microscopy, by detergent insolubility, or by failure to pass through a membrane of fixed pore size ("filter trap"). However, such methods are highly labor-intensive, can be prone to experimenter bias, and are not particularly quantitative. Recently Kim et al. used fluorescence resonance energy transfer (FRET) combined with single cell imaging to study the constituents of large macro-molecular aggregates in cultured cells (Kim et al., (2002). Nat Cell Biol 4, 826-831). This method, while providing relatively precise spatial resolution, is quite time- and labor-intensive, and does not quantify the degree of polyglutamine protein aggregation within a population of cells. Moreover, by focusing only on large inclusions, this and other microscopy-based approaches ignore small oligomeric micro-aggregates that can play an important role in pathogenesis (Taylor et al., (2003). Hum Mol Genet 12, 749-757). Currently there are no facile, high-throughput methods with which to identify cellular pathways and molecular mechanisms that regulate protein misfolding and aggregation in polyglutamine expansion diseases and other neurodegenerative diseases in animal cells, e.g., in situ.

SUMMARY OF THE INVENTION

Disclosed herein is a high throughput approach to identifying mechanisms and cellular regulation of aggregate formation. Included is a description of the development of this method, its use as a screening tool to identify protein aggregation regulators, and new insights into pathogenesis. Also disclosed are methods of treatment of protein aggregation diseases.

Accordingly, one aspect of the invention is a method for screening for modulators of protein aggregation, the method having the steps of providing at least one cell comprising a first protein linked to a FRET energy donor and a second protein linked to a FRET energy acceptor, wherein said first protein and said second protein aggregate; measuring a first FRET signal in the absence of a candidate compound; measuring a second FRET signal in the presence of a candidate compound; comparing the first FRET signal to the second FRET signal and identifying a modulator of protein aggregation as a candidate compound that results in a second FRET signal that is different from the first FRET signal. In one embodiment, the method for screening occurs in a multi-well plate as part of a high-throughput screen, e.g., it is an HTS method.

In preferred embodiments, the method for screening has a Z value of >0.5. In one embodiment, the method for screening has a Z value of about 0.67.

The method for screening employs, e.g., mammalian cells, e.g., HEK293 cells. In one aspect, the first and second proteins are polyglutamine proteins. In another aspect, the first and second proteins are, e.g., an AR, an htt, a tau protein, a synuclein, a superoxide dismutase, a PABPN1, an Aβ peptide, a serpin, a transthyretin, an ataxin, or a prion protein. In preferred embodiments, the first and second proteins are an htt or an AR.

The method employs methods for measuring FRET that are useful for HTS, e.g., the method employs a fluorescence plate reader (FPR) for detection of FRET.

As described above, the method of screening employs a protein that aggregates (e.g., AR) linked to a FRET donor and a FRET acceptor. In one embodiment, the FRET acceptor is CFP and the FRET donor is YFP. In one aspect, the method for screening has the steps of providing an HEK293 cell comprising AR linked to CFP and AR linked to YFP; measuring a first FRET signal in the absence of a candidate compound; measuring a second FRET signal in the presence of a candidate compound; wherein said first and second FRET signals are measured using a FPR; and comparing the first FRET signal to the second FRET signal and identifying a modulator of protein aggregation as a candidate compound that results in a second FRET signal that is different from the first FRET signal.

The invention also includes methods of modulating aggregation of a first protein in a cell by administering a sufficient amount of a protein aggregation regulator. The first can be a polyglutamine protein or the first protein can be, e.g., a tau protein, a synuclein, a superoxide dismutase, a PABPN1, an Aβ peptide, a serpin, a transthyretin, an ataxin, or a prion protein. In preferred embodiments, the first protein is an htt or an AR. In one embodiment, the method of modulating aggregation in a cell reduced aggregation by at least, e.g., 10% or at least 20% or at least 40%.

Protein aggregation regulators used in the methods of the invention include small molecules, antibodies and fragments thereof, peptides, and nucleic acids (e.g., genes, RNAi, antisense RNA, and the like). In one embodiment, the protein aggregation regulator is, e.g., a small molecule, e.g., Y-27632; or a gene, e.g., p160ROCK or a variant thereof. The effect of the protein aggregation regulator can be indirect, e.g., that regulator interacts with an upstream element of protein aggregation, e.g., p160ROCK, a rho-GTPase, a RhoA, a Cdc42, a Rac1, a Lim-1 kinase, a cofilin, or a slingshot phosphatase.

The protein aggregation regulator can have any number of effects in the cell, e.g., a caspase 1 inhibitor or, e.g., a kinase inhibitor. In one aspect of the invention, the protein aggregation regulator includes Ac-YVAD-cmk, Piceatannol, Compound 3, Compound 4, Iressa, Phalloidin, Jasplakinolide, WEHD-fmk, Hydralazine HCl, Carbachol, Chlorothiazide, Betahistine hydrochloride, Molsidomine, 1S,9R-beta hydrastin, Naringenin, Fosfosal, Diltiazem HCl, Nadolol, Spermidine HCl, Diffractic acid, Alaproclate, Leucodin, Arachidonic acid, or Minaprine HCl. Alternatively, the protein aggregation regulator modulates a target in a pathway, wherein said pathway is modulated by Ac-YVAD-cmk, Piceatannol, Compound 3, Compound 4, Iressa, Phalloidin, Jasplakinolide, WEHD-fmk, Hydralazine HCl, Carbachol, Chlorothiazide, Betahistine hydrochloride, Molsidomine, 1S,9R-beta hydrastin, Naringenin, Fosfosal, Diltiazem HCl, Nadolol, Spermidine HCl, Diffractic acid, Alaproclate, Leucodin, Arachidonic acid, or Minaprine HCl.

In one embodiment, the method reduces aggregation of an androgen receptor in a HEK293 cell by administering a sufficient amount of Y-27632.

As one embodiment of a method of modulating protein aggregation in a cell, the invention includes methods for treatment of a protein aggregation disease by administering to a patient in need of treatment a therapeutically effective amount of a protein aggregation regulator. In some aspects the method of treatment is for Huntington's disease (HD), spinobulbar muscular atrophy (SBMA), a tauopathy, an amyloid disease, Alzheimer's disease, a serpinopathy, systemic amyloidosis, ALS, ocularopharyngeal muscular dystrophy (OPMD), dominantly inherited spinocerebellar ataxias, or Parkinson's disease.

The method of treatment can employ, e.g., a small molecule, e.g., Y-27632. Alternatively, the method of treatment can employ, e.g., a gene, e.g., p160ROCK, slingshot phosphatase, or a variant thereof. In further embodiments, the protein aggregation regulator is, e.g., a caspase 1 inhibitor or, e.g., a kinase inhibitor. In other aspects, the protein aggregation regulator is Ac-YVAD-cmk, Piceatannol, Compound 3, Compound 4, Iressa, Phalloidin, Jasplakinolide, WEHD-fmk, Hydralazine HCl, Carbachol, Chlorothiazide, Betahistine hydrochloride, Molsidomine, 1S,9R-beta hydrastine, Naringenin, Fosfosal, Diltiazem HCl, Nadolol, Spermidine HCl, Diffractic acid, Alaproclate, Leucodin, Arachidonic acid, or Minaprine HCl.

The protein aggregation regulator may act directly or indirectly on protein aggregation. In one aspect, the protein aggregation regulator modulates a target in a pathway, wherein said pathway is modulated by Ac-YVAD-cmk, Piceatannol, Compound 3, Compound 4, Iressa, Phalloidin, Jasplakinolide, WEHD-fmk, Hydralazine HCl, Carbachol, Chlorothiazide, Betahistine hydrochloride, Molsidomine, 1S,9R-beta hydrastin, Naringenin, Fosfosal, Diltiazem HCl, Nadolol, Spermidine HCl, Diffractic acid, Alaproclate, Leucodin, Arachidonic acid, or Minaprine HCl. In another aspect, the protein aggregation regulator modulates an activity of a protein selected from the group consisting of a p160ROCK, a rho-GTPase, a RhoA, a Cdc42, a Rac1, a Lim-1 kinase, a cofilin, and a slingshot phosphatase.

BRIEF DESCRIPTION OF THE SEVERAL VIEWS OF THE DRAWING

These and other features, aspects, and advantages of the present invention will become better understood with regard to the following description, and accompanying drawings, where:

FIG. 1G, FIG. 1H, and FIG. 1I are standard fluorescence images taken on three channels (CFP, YFP, DAPI) and superimposed. Yellow results from co-localization of CFP and YFP. Images show the three characteristic polyglutamine protein distribution patterns (FIG. 1G) diffuse, (FIG. 1H) cytoplasmic inclusion and (FIG. 1I) nuclear inclusions. FIG. 1J, FIG. 1K, and FIG. 1L are calculated images that show the distribution of FRET efficiencies in the cells shown in (FIGS. 1G,H,I) based on applying the following formula to each pixel of the image: (CFPf−CFPi)/CFPf, where CFPi and CFPf are the CFP intensities before and after photobleaching of YFP, respectively. The resulting calculated gray-scale image was converted to colorscale using NIH-Image software. Note that diffuse protein had no significant increase in CFP signal following photobleaching whereas both nuclear and perinuclear aggregates had increased CFP signal, indicating FRET.

DETAILED DESCRIPTION OF THE INVENTION

Figure 1:
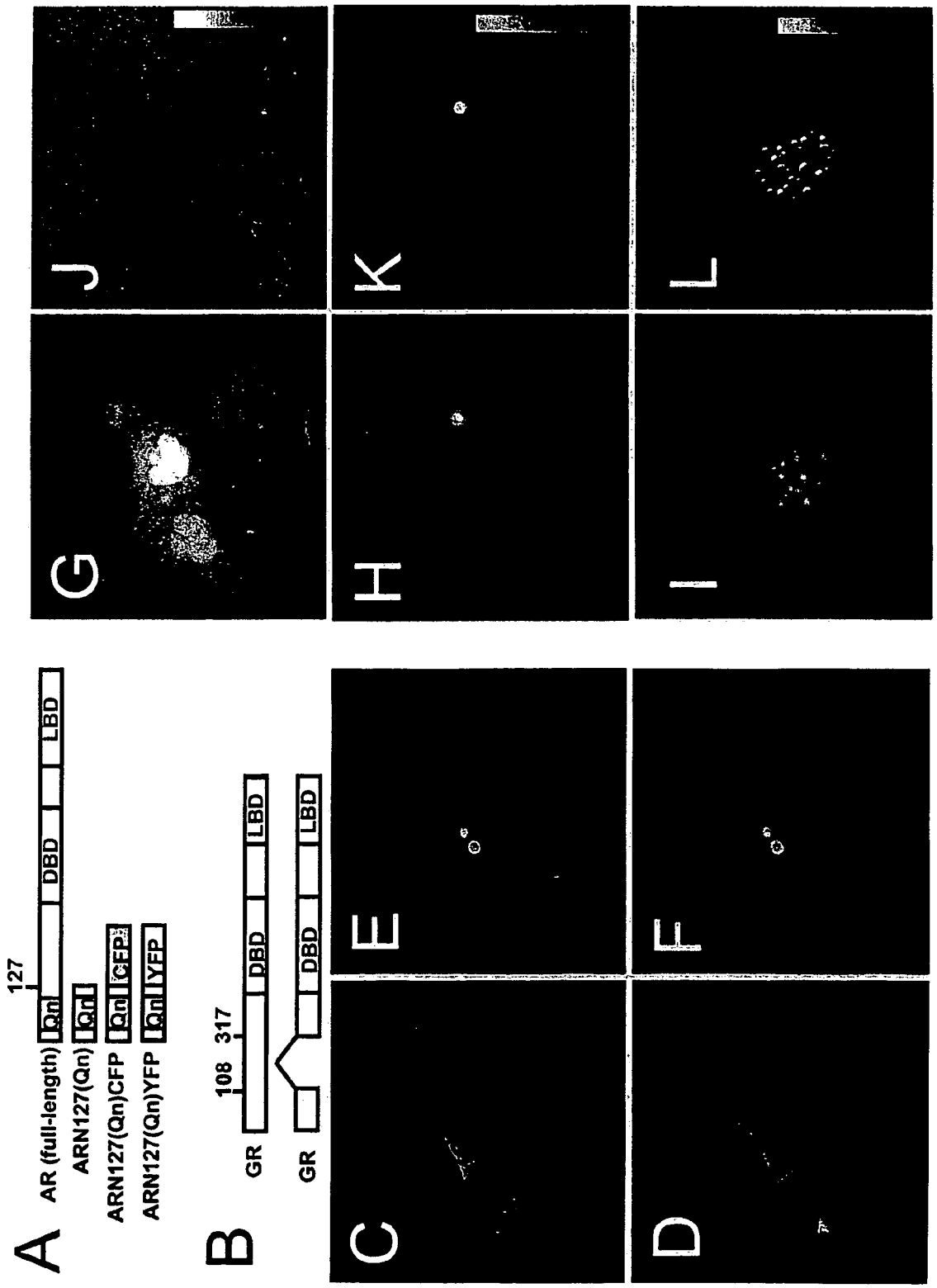
FIG. 1A is a figure of the AR constructs. The full length AR is shown for reference. Truncated forms contained the first 127 amino acids of AR (ARN127(Qn)) with either an unexpanded (n=25) or expanded (n=65) tract of glutamines. The truncated forms were fused to coding sequences of cyan and yellow fluorescent proteins (CFP and YFP, respectively). DBD=DNA binding domain. LBD=ligand binding domain.
FIG. 1B is a figure of the GR (glucocorticoid receptor) constructs, full length GR and GRΔ, which carries a deletion of an activation domain, amino acids 108-317. DBD=DNA binding domain. LBD=ligand binding domain.
FIG. 1C and FIG. 1D are images of differentiated C17-2 cells expressing ARN127(65)CFP/YFP in diffuse distribution, with tubulin stain included in FIG. 1D. Green signal represent polyglutamine protein, red represents a neuronal marker (tubulin) induced upon differentiation. Yellow color in FIG. 1D reflects super-imposition of red and green signals.
FIG. 1E and FIG. 1F are images of cells differentiated C17-2 cells expressing demonstrating nuclear aggregates, with tubulin stain included in FIG. 1F. Green signal represent polyglutamine protein, red represents a neuronal marker (tubulin) induced upon differentiation.
FIGS. 1G-L are images of diffuse and aggregated forms of AR and their qualitative FRET efficiencies in COS-7 cells coexpressing ARN127(65)CFP/YFP and GRΔ by transient transfection in the presence of 100 nM dex. Cells were fixed on coverslips and stained with DAPI.

Disclosed herein is a high-throughput screen (HTS) based on FRET that quantitatively measures protein aggregation within cultured cell monolayers. This assay overcomes the limitations of current technology of assaying cellular pathways and molecular mechanisms that regulate protein misfolding and aggregation in polyglutamine expansion and other protein aggregation diseases in cells. Further, the assay is useful in developing novel compounds, e.g., protein aggregation regulators, which target these pathways and mechanisms.

Also described herein are methods for modulation of protein aggregation, e.g., use of compounds identified by the HTS described herein as inhibitors of polyglutamine protein aggregation. Methods for ameliorating a protein aggregation disease using compounds identified by the protein aggregation assay are also disclosed.

One compound, Y-27632, was examined in further detail. A protein pathway implicated by Y-27632 was elucidated, and the efficacy of this compound in a *Drosophila* model of polyglutamine disease was tested. The disclosure demonstrates that Y-27632 is an inhibitor of protein aggregation via the Rho-activated serine/threonine kinase p160ROCK.

The use of FRET to study heterologous protein-protein interactions has been widely reported, including for polyglutamine proteins (Kim et al., (2002). Nat Cell Biol 4, 826-831; Sekar and Periasamy, (2003). J Cell Biol 160, 629-633). This is the first use of such technology to study intracellular protein interactions on a quantitative, high-throughput basis, in situ, entirely distinct from microscopy.

Several features of the current approach should be noted. By design it is not an assay of cell death or dysfunction, and is limited to detection of modifiers of protein folding and aggregation. Secondary screens (e.g., in stable cell lines, in *Drosophila* models, in mouse models) well known to those of skill in the art can be used to determine whether candidates have efficacy against cell dysfunction and death. The assay can be readily adapted for use with arrayed nucleic acid libraries, e.g., cDNA libraries, which require high transfection efficiency and robust protein expression, as the assay can employ, e.g., transfected non-neural cells (e.g., HEK293). In addition, polyglutamine aggregates in C17-2 neural cells can be detected via FRET, and use of stable neural cell lines expressing the CFP and YFP fusion proteins can increase detection of pathways relevant in vivo.

Finally, this in situ assay identified a compound functional in vivo in the *Drosophila* nervous system, demonstrating that non-neural cells have utility for studying basic mechanisms associated with protein misfolding and aggregation and identifying potential therapeutics for protein aggregation diseases.

Advantages of this HTS approach are numerous. Because the assay depends on particular molecular events—misfolding and aggregation—protein aggregation regulators identified by the assay are specific to this process. In contrast to microscopy-based methods that rely on analysis of macromolecular aggregation, this FRET-based method can produce signal even if aggregates have oligomeric structures that escape standard detection by microscopy.

Second, because the assay is cell-based, it can identify protein aggregation regulators that affect protein aggregation both directly and indirectly. This is in contrast to in vitro assays of protein aggregation, which are only capable of identifying direct modifiers of the protein of interest. Protein aggregation regulators that directly target polyglutamine proteins score in this assay, but so do compounds such as Y-27632, that modulate misfolding and aggregation indirectly through action on regulatory pathways.

Finally, this method is amenable to investigating neurodegenerative diseases about which there is little knowledge about the intracellular regulation of protein folding. In addition to using this method with polyglutamine proteins, it is readily amenable to study the regulation of folding of other aggregation-prone molecules responsible for neurodegenerative disease, such as tau, synuclein, superoxide dismutase, prion protein, and the like, e.g., this method can be used to study the regulation of extracellular protein aggregation.

The FRET-based assay system offers a new approach to identify regulatory mechanisms that control protein misfolding and aggregation in protein aggregation related diseases. It creates opportunities to screen chemical and genetic libraries, including arrayed cDNAs or siRNAs, in a high-throughput format in the context of intact cells, e.g., mammalian cells. The assay can provide leads in the development of treatments for patients with protein aggregation related diseases.

DEFINITIONS

Terms used in the claims and specification are defined as set forth below unless otherwise specified.

The term "ameliorating" refers to any therapeutically beneficial result in the treatment of a disease state, e.g., a protein aggregation disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

A protein aggregation regulator "modulates" protein aggregation means that a protein aggregation regulator has the effect of increasing or decreasing protein aggregation. This effect can be direct, e.g., the protein aggregation regulator directly interacts with the aggregated protein either before or during aggregation, or indirect, e.g., the protein aggregation regulator interacts with an upstream element, e.g., a gene or protein, that plays a role in the protein aggregation pathway.

The term "protein aggregation disease" includes those diseases in which protein aggregation plays a role. Such diseases are discussed in detail herein, and include but are not limited to polyglutamine expansion diseases such as, e.g., Huntington's disease (HD) and spinobulbar muscular atrophy (SBMA); tauopathies, e.g., Alzheimer's disease; amyloid diseases, e.g., Creutzfeld-Jacobson's disease, Alzheimer's disease, serpinopathies, and systemic amyloidosis; ALS; ocularopharyngeal muscular dystrophy (OPMD); dominantly inherited spinocerebellar ataxias; Parkinson's disease, and the like.

The term "protein aggregation regulator" refers to a compound that, when administered to a cell, modulates protein aggregation in the cell. A protein aggregation regulator can be, e.g., a small molecule, a gene, an antibody or fragment thereof, a peptide, or a nucleic acid, e.g., a gene, an antisense RNA, an antisense DNA, or an RNAi.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

Abbreviations used in this application include the following: ACL (Annotated Compound Library); RNA (ribonucleic acid); RNAi (inhibitory RNA); CFTR (cystic fibrosis transport regulator); ALS (amyotrophic lateral sclerosis); SMBA (spinobulbar muscular atrophy); AR (androgen receptor); HD (Huntington's disease); htt (huntingtin protein); YFP (yellow fluorescent protein); CFP (cyan fluorescent protein); GR (glucocorticoid receptor); dex (dexamethasone); PABPN1 (polyA binding protein nuclear 1); OPMD (oculaopharyngeal muscular dystrophy.

Methods of Screening for Protein Aggregation Regulators.

One aspect of the invention is a method of screening for modulators of protein aggregation, the method having the steps of providing at least one cell comprising a first protein linked to a FRET donor and a second protein linked to a FRET acceptor, wherein said first protein and said second protein aggregate; measuring a first FRET signal in the absence of a candidate compound; measuring a second FRET signal in the presence of a candidate compound; comparing the first FRET signal to the second FRET signal and identifying a modulator of protein aggregation as a candidate compound that results in a second FRET signal that is different from the first FRET signal. In one embodiment, the method for screening occurs in a multi-well plate as part of a high-throughput screen, e.g., it is an HTS method.

The methods disclosed are useful for identifying and testing compounds, e.g., protein aggregation regulators, useful for treatment of diseases involving protein aggregation, e.g., polyglutamine expansion diseases.

In preferred embodiments, the method for screening has a Z value of >0.5. In one embodiment, the method for screening has a Z value of about 0.67.

The method of screening is performed in situ, e.g., in a cell outside of a living organism, e.g., in tissue culture. The wide range of tissue culture techniques are well known to one of skill in the art and can be found in a variety of references including, e.g., Basic Cell Culture: A Practical Approach. J. Davis, Oxford University Press (2002) 416 pp. 2nd edition. Methods performed in situ can be performed in any standard tissue culture vessel well known to one of skill in the art. Examples include but are not limited to, e.g., dishes, bottles, trays, microtiter plates, and the like. In a preferred embodiment, the method is performed in microtiter plates to facilitate high throughput screening of libraries of potential protein aggregation regulators.

The methods of the invention are performed in a cell. In one embodiment, the cells are mammalian cells, e.g., human cells. Examples include but are not limited to COS-7 cells and HEK293 cells. The cells can be neuronal cells, e.g., C17-2 neural precursor cells, PC-12 cells, or transfected primary neuronal cells. In preferred embodiments, the cells are HEK293 cells.

The term "cells" encompasses invertebrate, non-mammalian vertebrate (e.g., avian, reptile and amphibian) and mammalian cells. Examples of invertebrate cells include the following insect cells: *Spodoptera frugiperda* (caterpillar), *Aedes aegypti* (mosquito), *Aedes albopictus* (mosquito), *Drosophila melanogaster* (fruitfly), and *Bombyx mori*. See, e.g., Luckow et al., Bio/Technology, 6:47-55 (1988); Miller et al., in Genetic Engineering, Setlow, J. K. et al., eds., Vol. 8 (Plenum Publishing, 1986), pp. 277-279; and Maeda et al., Nature, 315:592-594 (1985).

Examples of mammalian cells include monkey kidney CV1 line transformed by SV40 (COS-7, ATCC CRL 1651); human embryonic kidney line (293 or 293 cells subcloned for growth in suspension culture, Graham et al., J. Gen Virol., 36:59 [1977]); baby hamster kidney cells (BHK, ATCC CCL 10); Chinese hamster ovary cells/–DHFR(CHO, Urlaub and Chasin, Proc. Natl. Acad. Sci. USA, 77:4216 [1980]); mouse sertoli cells (TM4, Mather, Biol. Reprod., 23:243-251 [1980]); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 [1982]); MRC5 cells; FS4 cells; and a human hepatoma line (Hep G2).

The screening method of the invention can use any suitable protein that aggregates, well known to one of skill in the art. Both polyglutamine expansion proteins and non-polyglutamine expansion proteins can be used. Polyglutamine expansion proteins include but are not limited to htt and AR and in a preferred embodiment, the screening methods of the invention use htt or AR. Non-polyglutamine expansion proteins that can be used in the methods of the invention include but are not limited to, e.g., a tau protein, a synuclein, a superoxide dismutase, a prion protein, a PABPN1, an Aβ peptide, a serpin, a transthyretin, an ataxin, or a prion protein.

In one embodiment, the screening method detects modulation of protein aggregation occurring inside the cell. In alternative embodiments, the screening method is used to detect modulation of protein aggregation occurring outside of the cell, e.g., extracellularly.

Protein aggregation based on FRET is measured, e.g., monitored, using a quantitative method, e.g., a monochrometer-based fluorescence plate reader (FPR). FRET can be measured using either emission scans or fixed "windows" measurements that are analogous to "three filter set" methods used commonly in microscopy. The use of FPR is advantageous as it allows simultaneous measurements from thousands of cells grown as a monolayer in the bottom of a 96-well plate, and can readily discriminate cells with aggregated vs. diffusely distributed protein.

As described above, the method of screening employs a protein that aggregates (e.g., AR) linked to a FRET energy donor and a FRET energy receptor. Any number of FRET donor/acceptor pair known to one of skill in the art can be used. In one embodiment, the FRET energy donor is YFP and the FRET energy acceptor is CFP.

Methods for Modulating Protein Aggregation in Cells

The invention provides methods for modulating protein aggregation in a cell by administering a sufficient amount of a protein aggregation regulator. The methods disclosed are useful for studying cellular pathways of protein aggregation, and for testing compounds, e.g., protein aggregation regulators, useful for treatment of diseases involving protein aggregation, e.g., polyglutamine expansion diseases. The invention also provides methods for treatment of a protein aggregation disease, e.g., Huntington's disease or SBMA, by administering to a patient in need of treatment a therapeutically effective amount of a protein aggregation regulator.

In one embodiment, the methods are performed in situ, e.g., in a cell outside of a living organism, e.g., in tissue culture. Any number of cells well known to one of skill in the art are suitable for the method. In one aspect, the method employs, e.g., mammalian cells, e.g., HEK293 cells.

In another embodiment of the invention, the method is performed in vivo, e.g., in a living organism. Living organisms include invertebrates, non-mammalian vertebrates, and mammals. The method can be performed in both non-human and human mammals. In a variation of the invention, the method is performed in fly, worm, zebrafish, rat, and mouse models of a polyglutamine disease. In one embodiment, the methods are performed in a Drosophila model of Huntington's disease, e.g., Drosophila neuronally expressing an htt exon 1 fragment. In another embodiment, the methods are performed in mouse models, e.g., AR112 or, e.g., R6/2.

As discussed above, a wide variety of proteins aggregate and play a role in disease, especially neurodegenerative diseases. The methods of the invention can be used to modulate aggregation of any of these proteins, well known to one of skill in the art. Examples include both polyglutamine expansion proteins and non-polyglutamine expansion proteins. In a preferred embodiment, the methods of the invention are used to modulate aggregation of the AR. In another preferred embodiment, the aggregation of htt is modulated.

The methods of the invention include using an effective amount of the protein aggregation regulator. An effective amount is an amount that changes protein aggregation by, e.g., at least 10%, at least 20%, or at least 40% as compared to the protein aggregation in the cell in the absence of protein aggregation regulator. The change in protein aggregation is determined using the assays described herein, e.g., in situ FRET assays.

Other methods of the invention employ use of a therapeutically effective amount of the protein aggregation regulator. A therapeutically effective amount is an amount that ameliorates, e.g., lessens the timecourse or severity of the protein aggregation disease, including remission or cure thereof. Determination of a therapeutically effective amount is discussed in more detail below, under "Pharmaceutical compositions of the invention."

Protein Aggregation Regulators

Disclosed herein are methods for discovery of protein aggregation regulators, and the invention provides methods of using a protein aggregation regulator for modulating protein aggregation in a cell. A protein aggregation regulator is a compound that, when administered to a cell, modulates protein aggregation in the cell. A protein aggregation regulator can be, e.g., a small molecule, an antibody or fragment thereof, a peptide, or a nucleic acid, e.g., a gene, an antisense RNA, or an RNAi. Libraries of these potential protein aggregation regulators are well known to one of skill in the art. These libraries can be screened using the methods described herein to identify those compound that modulate protein aggregation. Briefly, this screen utilizes cells, e.g., HEK293 cells, expressing an aggregation protein, e.g., AR, linked to both a FRET donor and FRET acceptor, e.g., CFP and YFP. The CFP-AR and YFP-AR are both expressed in the same cell, and aggregation of AR is monitored by an increase in FRET as measured using, e.g., a monochrometer-based fluorescence plate reader (FPR). Cells are cultured in both the absence and presence of a test compound, and FRET measurements are compared. A test compound that produces a difference, e.g., reduction, in aggregation is characterized as a potential protein aggregation regulator.

Disclosed herein is screening of a three libraries: a small chemical library (ACL); a library of kinase inhibitors; and the NINDS library. In one embodiment, methods of the invention employ compounds from these libraries that exhibit inhibition in both a primary (e.g., HTS) and secondary screen using the AR FRET assay are one embodiment of the invention, e.g., Ac-YVAD-cmk, Piceatannol, Compound 3, Compound 4, Iressa, Phalloidin, Jasplakinolide, WEHD-fmk, Hydralazine HCl, Carbachol, Chlorothiazide, Betahistine hydrochloride, Molsidomine, 1S,9R-beta hydrastin, Naringenin, Fosfosal, Diltiazem HCl, Nadolol, Spermidine HCl, Diffractic acid, Alaproclate, Leucodin, Arachidonic acid, and Minaprine HCl. In another embodiment, the protein aggregation regulator used in the methods of the invention is Y-27632.

Additional protein aggregation regulators can be designed beginning with the compounds that demonstrate modulation of protein aggregation using the methods described herein. For example, Y-27632 can be used as a starting point to define a detailed chemical species that more potently inhibits polyglutamine aggregation. A systematic modification of sidechains with a variety of chemical moieties is performed. Using the FRET-based screen, such modified compounds are assayed for activity as inhibitors of aggregation. More potent inhibitors are studied in greater detail in cell, Drosophila, and mouse models of protein aggregation, e.g., polyglutamine expansion, diseases.

The FRET based assay described herein is used to screen for protein aggregation regulators that modulate protein aggregation. Modulation can be either increasing or decreasing protein aggregation. In one embodiment, a protein aggregation regulator directly interacts with the protein that aggregates (e.g., htt or AR) either before or during aggregation. In another aspect of the invention, the protein aggregation regulator modulates aggregation indirectly, e.g., the protein aggregation regulator interacts with a gene or gene product that plays a role in the protein aggregation pathway.

In one aspect of the invention, the protein aggregation regulator modulates the activity of at least one protein that regulates the protein aggregation of, e.g., htt or AR. Examples include but are not limited to p160ROCK, a rho-GTPase, a RhoA, a Cdc42, a Rac1, a Lim-1 kinase, a cofilin, and a slingshot phosphatase. In a preferred embodiment, the protein aggregation regulator modulates the activity of p160ROCK. In another aspect, the protein aggregation regulator is a variant of a gene that plays a role in the protein aggregation pathway, e.g., the protein aggregation regulator is a dominant negative mutant of p160ROCK.

The assay described herein is particularly useful for elucidating the cellular pathways involved in protein aggregation, thereby useful for identifying potential therapeutics and therapeutic targets. For example, and as disclosed in more detail below, the effect of the drug Y-27632 on protein aggregation was approximated by over-expressing a dominant negative p160ROCK mutant, p160ROCK(KD-IA). Potential upstream regulators of p160ROCK (RhoA, Rac1, and Cdc42) were also assayed, using the FRET based protein aggregation assay described herein. A dominant positive Rac1 mutant increased polyglutamine protein aggregation, whereas a dominant negative form inhibited this process. Furthermore, a mutation in Rac1 that blocks its interaction with p160ROCK also eliminated the effects of Rac1 on polyglutamine aggregation.

The effects of the Rac1 mutants together with Y-27632 demonstrate a significant role of p160ROCK and the cytoskeleton in the regulation of aggregation. Without being bound by theory of mechanism, the effects of RhoA and Cdc42 on polyglutamine aggregation are likely due to cross-talk between these pathways, in which one rho-GTPase may modulate the activity of another (Etienne-Manneville and Hall, (2002) Rho GTPases in cell biology. Nature 420, 629-635; Hirose et al., (1998) Molecular dissection of the Rho-associated protein kinase (p160ROCK)-regulated neurite remodeling in neuroblastoma N1E-115 cells. J Cell Biol 141, 1625-1636).

Pharmaceutical Compositions of the Invention

Methods for treatment of protein aggregation diseases are also encompassed by the present invention. Said methods of the invention include administering a therapeutically effective amount of a protein aggregation regulator. The protein aggregation regulator of the invention can be formulated in pharmaceutical compositions. These compositions can comprise, in addition to one or more of the protein aggregation regulators, a pharmaceutically acceptable excipient, carrier, buffer, stabiliser or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

Whether it is a polypeptide, antibody, nucleic acid, small molecule or other pharmaceutically useful compound according to the present invention that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

EXAMPLES

Methods

Plasmid Construction

To construct ARN127-CFP and ARN127-YFP fusion proteins, coding sequences for ECFP and EYFP were PCR amplified from pECFP.C1 and pEYFP.C1 (Clontech) and were cloned downstream of ARN127 sequence into p6RARN127 (Diamond et al., (2000). Proc Natl Acad Sci 97, 657-661), to form p6RARN127(Qn)CFP or p6RARN127(Qn)YFP, with n=25 or 65 CAG repeats. To construct the YFP-CFP fusion protein, an intermediate vector was constructed in which the HincII/BsrG1 fragment of pEYFP (Clontech) containing the coding region for YFP was placed into the Eco47III/BsrG1 backbone of pEGFP-C1 (Clontech) to excise EGFP and create a vector with a polylinkers on both 3' and 5' sides of the EYFP coding region. Then the BamHI fragment of this vector was subcloned into the BamH1/BglII backbone on ECFP-N3 to place EYFP in-frame and 5' to ECFP.

To construct htt exon 1-CFP and -YFP fusions, htt exon 1 fragment derived from plasmid qp72 (a gift from A. Kazantsev) was subcloned as a SalI/BamHI fragment, replacing the ARN127 coding sequence in p6RARN127CFP/YFP to form p6Rhtt(72)CFP and p6Rhtt(72)YFP.

Expression of each protein was driven by the constitutive RSV promoter (Diamond, M. I., Robinson, M. R., and Yamamoto, K. R. (2000). Proc Natl Acad Sci 97, 657-661).

Plasmid encoding p160ROCK(KD-IA) was kindly provided by S. Narumiya. Plasmids encoding dominant positive and negative rho-GTPase mutants (RhoA, Rac1, Cdc42) were obtained from the cDNA Resource Center at the Guthrie Research Institute (Sayre, Pa. 18840). F37A and Y40C mutations in V12Rac were introduced by site-directed mutagenesis.

Cell Culture and Transfection

For photobleaching experiments, COS-7 cells were transfected on coverslips in 6-well dishes. Each well was transfected with 1 µg of a mixture of AR127(65)CFP/YFP and 1 µg GRΔ using 10 µL Plus™ and 12 µL Lipofectamine™ according to manufacturer's protocol (Invitrogen). After 5 hours, transfection medium was replaced with complete medium containing 100 nM dex, and cells were cultured for 48 hours to allow aggregate formation.

For experiments in the fluorescence plate reader, high-throughput screening, and detergent fractionation, HEK293 cells in 6-well plates were transfected with a total of 2 µg of DNA using 10 µL Plus™ and 12 µL Lipofectamine™ according to manufacturer's protocol. To control for autofluorescence and light scattering by mammalian cells, a control group was transfected with 2 µg pcDNA3. To control for bleedthrough and crossover excitation, CFP and YFP controls were transfected with 1 µg pECFP-C1 (Clontech) and 1 µg pcDNA3 (Invitrogen) or 1 µg pEYFP-C1 (Clontech) and 1 µg pcDNA3 respectively. After 5 hours, cells were counted and plated into optically clear 96-well plates (Costar™ 3603) at a density of 60,000 cells/well. For assays of p160ROCK(KD-IA), it was necessary to reduce the amount of this plasmid by 80% due to toxicity at higher levels: 0.2 µg p160ROCK(KD-IA), 0.8 µg pcDNA3, and 1 µg of either 6RARN127(65)CFP/YFP or 6Rhtt(72)CFP/YFP were used. For assays of rho-GTPase mutants, 1 µg of each was used in conjunction with 1

µg of the polyglutamine expression plasmids. Transfections were performed in triplicate, and each experiment was repeated 6 times. C17-2 neural precursor cells were plated in 12-well plates and transfected using 4 µg of DNA and 4 µl of Lipofectamine 2000™. 16 hours following transfection, cells were replated on coverslips coated with poly-L-lysine and laminin, and grown in DME-H21 supplemented with 1% fetal bovine serum and 100 ng/ml each of NGF and mitomycin for two days. In C17-2 cells polyglutamine protein was visualized by direct fluorescence; neuron-specific tubulin was visualized by immunostaining with mouse monoclonal antibody Neuro TUJ1 (Covance) at 1:1000.

Deterrent Fractionation

To measure effects of GR and GRΔ, HEK293 cells were cultured in 3.5 cm wells and transfected with 1 µg of total DNA consisting of 0.5 µg of ARN127(Q25/65)YFP and 0.5 µg of p6RGR or p6RGRΔ. Cells were cultured in the presence or absence of 100 nM dexamethasone (dex) for 48 hours. For titration of Y-27632, cells were transfected with ARN127(65) CFP/YFP alone, and cultured with the indicated amounts of drug. Cells were harvested by washing off the plate in PBS/5 mM EDTA, gentle centrifugation, and freezing of the pellets. Cell pellets were stored at −20° C. until future use. At this time, ice-cold lysis buffer was prepared consisting of PBS with 1% TRITON® X-100 (Sigma) and 1 µg/ml each of aprotinin, leupeptin, and pepstatin (Sigma). Pellets were resuspended in 400 µl of lysis buffer, and lysis performed by 10-15 passages through a 26 g needle to break up nuclei and shear chromatin. The lysate was centrifuged at 15,000×g for 5 minutes at 4° C. 100P of the supernatant was removed, and the remainder discarded. The pellet was then washed 1× with lysis buffer and again centrifuged at 15,000×g. The pellet was then resuspended in 50 µl of SDS sample buffer and boiled for 10 minutes. Total protein was determined in each supernatant fraction according to the Bradford method, and fractions representing equivalent amounts of total protein were diluted into SDS sample buffer. Equivalent proportions of the pellet fractions were also diluted into SDS sample buffer, and samples were resolved by electrophoresis on a 10% polyacrylamide gel. After transfer to a nylon membrane, immunoblotting was performed using rabbit N-20 anti-AR antibody at 1:2000 dilution (Santa Cruz Biotechnology). Following secondary antibody incubation, blots were developed using chemiluminescent substrate and exposure to x-ray film. Densitometry scans were performed on the film using NIH Image 1.62 software. These experiments were repeated at least six times with similar results.

Detection of Fret Via Photobleaching of Fixed Cells

Fixed COS-7 cells on coverslips were mounted in 50% glycerol/PBS without bleach retardant 48 hours after transfection. All images were obtained using a 60×1.4 N.A. lens (Olympus, Lake Success, N.Y.) and n=1.518 immersion oil. Digital images were acquired using a 12-bit cooled charged-coupled device on a multiwavelength wide-field optical sectioning microscopy system (Deltavision™, Applied Precision, Issaquah, Wash.). Channels used for imaging were as follows: CFP: exciter D436/10, JP4 beamsplitter, emitter D470/30; YFP: exciter HQ500/14, JP4 beamsplitter, emitter HQ535/30 (Chroma Technology Corp., Brattleboro, Vt.). To create an image in which the intensity reflected an estimate of FRET efficiency, on a pixel-by-pixel basis the value of the initial CFP image was subtracted from the final CFP image obtained after photobleaching, and this difference was multiplied by 100 and divided by the final CFP image intensity: $100 \times (CFP_{final} - CFP_{initial})/CFP_{final}$. Image arithmetic was performed using Deltavision™ software and converted from gray-scale to color using NIH-Image 1.62 software.

Detection of Fret Via Three Filter Measurements

For FRET detection in C17-2 cells via three filter set measurements, fixed cells on coverslips were analyzed by direct fluorescence microscopy. All images were collected using an Olympus 60× Plan Apochromat objective and quantitative fluorescence microscopy equipment as previously described (Schaufele et al., (2003). J Biol Chem 278, 10578-10587; Weatherman et al., (2002). Mol Endocrinol 16, 487-496). For each cell, three fluorescence channels were collected: the donor channel consisted of CFP excited with 431-440 nm light and CFP fluorescence collected at 455-485 nm; the acceptor channel consisted of YFP excited with 496-505 nm light and YFP fluorescence collected at 520-550 nm; and the FRET channel consisted of CFP excited with 431-440 nm light and YFP fluorescence collected at 520-550 nm. Cells separately expressing ARN127(65)CFP and ARN127(65) YFP were used to determine the separate contributions of the donor and acceptor fluorophores to each channel for both diffuse and aggregated protein.

Emission Scans on the Fluorescence Plate Reader (FPR)

After 48-hours in culture, cells were fixed for 2 minutes in 10% formaldehyde/PBS, the formaldehyde was replaced with 200 µL per well of PBS, and the cells were read on a fluorescence plate reader (SAFIRE, Tecan, Inc.). Automated scans were performed in which each well was excited at 435±2.5 nm while monitoring emission from 455±6 nm to 600±6 nm (FRET scan) to record CFP and FRET signals and then excited at 485±2.5 nm while monitoring emission from 500±6 nm to 600±6 nm (YFP scan) to record YFP signal. Data were analyzed as follows. First, the averaged signals from wells transfected with vector alone were used to background subtract all other signals. To normalize for CFP expression, a control sample transfected with CFP alone was used. Sample 435 nm and 485 nm emission curves were multiplied by the ratio of control CFP signal to sample CFP signal in the window 482 nm-492 nm, following 435 nm excitation: $N_{CFP} = CFP_{control}/CFP_{sample}$. After such normalization, subtraction of the CFP control curve from the sample curve removes the contribution of CFP bleedthrough from the sample FRET scan. To adjust for YFP crossover activation, a control sample transfected with YFP alone was used. The control YFP control signal (em 520-530 nm) from 435 nm excitation was divided by the YFP control signal following 485 nm excitation to determine the following crossover activation ratio: $X_{YFP} = (YFP_{ex435/em520-530}/YFP_{ex485/em520-530})$. With this information, it is possible to subtract out the contribution of YFP crossover activation to the FRET signal. The resulting curve contains emission solely due to FRET: $FRET_{calc} = \{N_{CFP} \times (Sample_{ex435})\} - (CFP\ control_{ex435}) - \{N_{CFP} \times (Sample_{ex485}) \times X_{YFP}\}$ FRET Measurements Using Fixed Excitation/Emission Windows Automated measurements of each well were taken on the FPR using the following three windows: CFP ex 435±2.5 nm/em: 485±6 nm; FRET ex 435±2.5 nm/em 485±6 nm; YFP ex 485±2.5 nm/em: 530±6 nm. Data were analyzed as follows. All readings were background subtracted based on averaged readings from cells transfected with vector alone. Controls containing CFP alone were used to normalize sample readings in all three windows by the ratio of control-to-sample signal in the CFP window: $N_{CFP} = CFP_{control}/CFP_{sample}$. After this normalization, subtraction of CFP control signal in the FRET window from sample signal in the FRET window removes the contribution of CFP bleedthrough from the sample signal. Control samples containing YFP alone were used to characterize YFP crossover excitation as a percentage of signal in the YFP window that appeared the FRET window: $X_{YFP}=YFP_{FRET}/YFP_{YFP}$. Subtraction of this percentage of the sample signal in the YFP window from the sample signal in the FRET window removes the contribution of crossover excitation from the sample FRET signal. The remaining signal is due solely to FRET. $FRET_{calc}=(N_{CFP}\times Sample_{435/530})-(Pure\ CFP_{435/530})-\{(N_{CFP}\times(Sample_{485/530})\times X_{YFP}\}$ High-Throughput Screen Using AR Selected candidate compounds and/or libraries of compounds were screened as follows. Daughter plates were created in duplicate from the 384-well microtiter plates that contained the compounds at a concentration of 80 µg/ml. Compounds were aliquoted in 96-well plates (Costar™ 3603) at a concentration at which most of the compounds are active, but are not toxic to the cells (e.g., of 4 µg/ml). To screen a library, HEK293 cells stably expressing RFP were plated in 10 cm plates to obtain ~80% confluency on the day of transfection. Each plate was transfected with 2 µg of ARN127(65) CFP/YFP each, and 0.7 µg p6RGRΔ using 50 µL Plus Reagent™ and 76 µL Lipofectamine™ according to manufacturer's protocol (Invitrogen). After 3 hours, complete medium was added and the plates were incubated further for 3 hours. Next, after adding 100 nM dex, the cells were counted and plated at a density of 70,000 cells/well in duplicate 96-well daughter plates containing single aliquots of compounds. The cells were then cultured for ~48 hours to allow aggregate formation. After fixing the cells FRET signal was measured using a SAFIRE Fluorescence Plate Reader (Tecan, Inc.) according to methods described above. Several internal controls were used to standardize each experiment. Mock transfected cells were used to control for background autofluorescence and light scattering by mammalian cells. To control for CFP bleedthrough and crossover excitation of YFP, additional wells contained cells expressing ARN127 (25)CFP or ARN127(25)YFP alone. RFP was measured to control for non-specific effects on steady-state protein levels. ARN127(25)CFP/YFP expression served as a reference point for background FRET levels without aggregation (a theoretical maximum effect on aggregation inhibition). FRET measurements for each experiment were thus scaled between 100% (cells with no drug treatment) and 0% (FRET levels from unexpanded protein). Last, each plate also contained wells treated with Y-27632 (50 µM) as a positive control.

FRET Based Assay of htt Aggregation

Aggregation of htt was monitored using the FPR FRET based HTS described herein for assaying aggregation of AR, using plasmids with htt exon 1-CFP and -YFP fusions containing 72 repeats (htt(72)CFP/YFP). HEK293 cells were transfected with htt(72)CFP/YFP as above, and cells were plated into a 96-well dish in the presence or absence of various concentrations of test compounds. After 24 hours, cells were fixed in 4% paraformaldehyde, and FRET signal was determined from the cell monolayers by reading on the FPR.

Assay of Candidate Compounds on Neurodegeneration in *Drosophila*

Transgenic flies were used, harboring a human huntingtin exon 1 fragment with 93 glutamines (htt exon 1 (Q93)) that is expressed in all fly neurons under the control of the elav:Gal4 driver. Flies expressing the transgene display progressive degeneration of the photoreceptor neurons, which is revealed by a time-dependent decrease in the number of rhabdomeres per ommatidium (Steffan et al., (2001). Nature 413, 739-743.) Normal fly eyes have seven visible rhabdomeres, while flies expressing htt exonl (Q93) display reduced numbers of rhabdomeres.

Flies were treated by maintaining adults on food containing candidate compound (e.g., 25 µM Y-27632) or no drug supplement. The number of rhabdomeres in treated vs. untreated flies were analyzed seven days post-eclosion by the pseudopupil technique as described (Steffan et al., (2001). Nature 413, 739-743). Approximately 50-60 ommatidia were analyzed for rhabdomere content on each of 10-12 flies from each treatment group, and the average number of rhabdomeres per ommatidium in each individual was determined. Percent rhabdomere loss was calculated as 100×((7−average number remaining)/7) before and after treatment.

Cell Model of Full Length AR Cytopathology.

Immortalized cell lines were created expressing full-length AR that differentiated in vitro into cells that resemble CNS neurons. C17.2 cells were used, developed by Evan Snyder, M. D., Ph.D. which are a transformed mouse neural precursor cell line that retain the ability to engraft and differentiate into CNS neurons and glia when implanted into fetal mouse brain (Snyder et al. 1192 Cell 68:33-51). In their undifferentiated form these cells may be propagated and easily transfected in vitro. However, upon serum starvation, addition of growth factor (NGF 100 ng/ml), and mitomycin (100 ng/ml) they differentiate into cells that have many features of CNS neurons, including axons, dendrites, and expression of neuron-specific markers.

C17.2 cell lines were created that stably expressed full-length HA-tagged forms of AR (25, 66, 103, or 122 glutamines). These AR(n)-C17.2 cell lines recapitulate several important aspects of SBMA, including proteolytic cleavage, and nuclear inclusion formation (data not shown). In their undifferentiated form, these cells showed no evidence of polyglutamine toxicity with or without DHT administration, which is now known to initiate the toxicity of full-length expanded AR in vivo (Katsuno et al. 2002 Neuron 35:843). After six days of differentiation, AR(25)-C17.2 cells cultured with or without DHT readily formed neuron-like cells, expressing neural markers and extending long axonal processes. In contrast, AR(122)-C17.2 cells had markedly reduced numbers of surviving neurons.

To assay the effects of candidate compounds, stable C17-2 neural cell lines expressing AR(25), AR(66), or AR(103) are cultured with or without 100 nM DHT and with or without candidate compounds (e.g., 50 µM Y-27632). To determine the effect on AR levels in stable cells, western blots are performed using AR or tubulin (control) antibodies. DHT increases AR steady-state levels. To determine the effect on polyglutamine toxicity, cells are examined by microscopy after 6 days of differentiation to determine numbers of surviving neurons, as indicated by red labeling of neuron-specific tubulin.

Pharmacokinetics of Candidate Compounds

The pharmacokinetics of candidate compounds were assayed in serum and brain of mice. Wild-type C57B6 mice are injected with a single IP dose of a candidate compound, e.g., Y-27632 at 10 mg/kg. Pairs of animals are sacrificed at various time points and serum and brain samples were obtained for LC-MS analysis of drug levels. Plots of serum concentration vs. time and brain concentration vs. time are used to analyze, e.g., penetration of the blood/brain barrier, drug kinetics, and $t_{1/2}$.

Example 1

Aggregated Pollglutamine Proteins Produce FRET when Fused to Fluorescent Proteins A screening assay was developed using an amino-terminal 127-amino acid fragment of AR containing either 25 glutamine repeats (ARN127 (25)) or a pathologic expanded tract of 65 repeats (ARN127 (65)). These polypeptides were fused at their carboxyl-termini either to CFP or YFP coding sequences (FIG. 1A). Similar truncated AR gene products have previously been shown to reproduce a neurodegenerative phenotype in transgenic animals and cell models (Abel, A., et al (2001) Hum Mol Genet 10, 107-116; Merry et al., (1998) Hum Mol Genet 7, 693-701; Welch and Diamond, (2001) Hum Mol Genet 10, 3063-3074). When expressed transiently in mammalian cells, the unexpanded forms of the protein (ARN127(25)CFP/YFP) remained diffusely distributed throughout the cytoplasm (data not shown). In contrast, the expanded proteins (ARN127(65)CFP/YFP) spontaneously formed perinuclear or nuclear aggregates.

FRET was initially measured in transfected non-neural and neural cells by two distinct microscopy-based methods. First, photobleaching was used to test whether aggregate-containing cells might be distinguished from those with soluble protein based on differences in their FRET signals. When FRET occurs, photobleaching the acceptor (YFP) molecule increases donor (CFP) emission. For ease in imaging, COS-7 cells were transfected with ARN127(65)CFP/YFP and GRΔ to create a population of cells with diffuse protein, or either cytoplasmic or nuclear aggregates. Individual cells were examined under a microscope, and quantified CFP emission before and after photobleaching YFP, using digital photography to record fluorophore intensities. Photobleaching increased CFP emission from either cytoplasmic or nuclear inclusions an average of about 20%, but not from diffusely distributed protein (FIGS. 1G-L). In cells expressing unexpanded protein there was no aggregation, and no FRET signal was detected. Similar results were also obtained in HEK293 cells (data not shown).

To confirm that polyglutamine aggregates would produce FRET in neural cells, differentiated C17-2 neural precursor cells were employed (Snyder et al., (1992). Cell 68, 33-51) (FIG. 1C-F). In this case FRET was measured according to a three filter set method, which corrects for CFP bleedthrough into the YFP spectrum, and crossover activation of YFP by CFP excitation. (Schaufele et al., (2003) J Biol Chem 278, 10578-10587; Weatherman et al., (2002) Mol Endocrinol 16, 487-496). FRET in cells was measured with nuclear aggregates vs. those with diffuse distribution of protein. Whereas diffusely distributed protein produced no significant FRET signal (FRET/CFP=0.023+/−0.041, n=8), nuclear aggregates had clear FRET signal (FRET/CFP=0.176+/−0.78, n=19). Thus, by separate methods in neural and non-neural cells, both nuclear and cytoplasmic inclusions produced strong FRET, whereas diffusely distributed protein did not.

FIG. 1G, FIG. 1H, and FIG. 1I are standard fluorescence images taken on three channels (CFP, YFP, DAPI) and superimposed. Yellow results from co-localization of CFP and YFP. Images show the three characteristic polyglutamine protein distribution patterns (FIG. 1G) diffuse, (FIG. 1H) cytoplasmic inclusion and (FIG. 1I) nuclear inclusions. FIG. 1J, FIG. 1K, and FIG. 1L are calculated images that show the distribution of FRET efficiencies in the cells shown in (FIGS. 1G,H,I) based on applying the following formula to each pixel of the image: (CFPf-CFPi)/CFPf, where CFPi and CFPf are the CFP intensities before and after photobleaching of YFP, respectively. The resulting calculated gray-scale image was converted to color-scale using NIH-Image software. Note that diffuse protein had no significant increase in CFP signal following photobleaching whereas both nuclear and perinuclear aggregates had increased CFP signal, indicating FRET.

Example 2

Detection of FRET Signal in Cell Monolayers Using Emission Scans in a Fluorescence Plate Reader (FPR)

Figure 2:
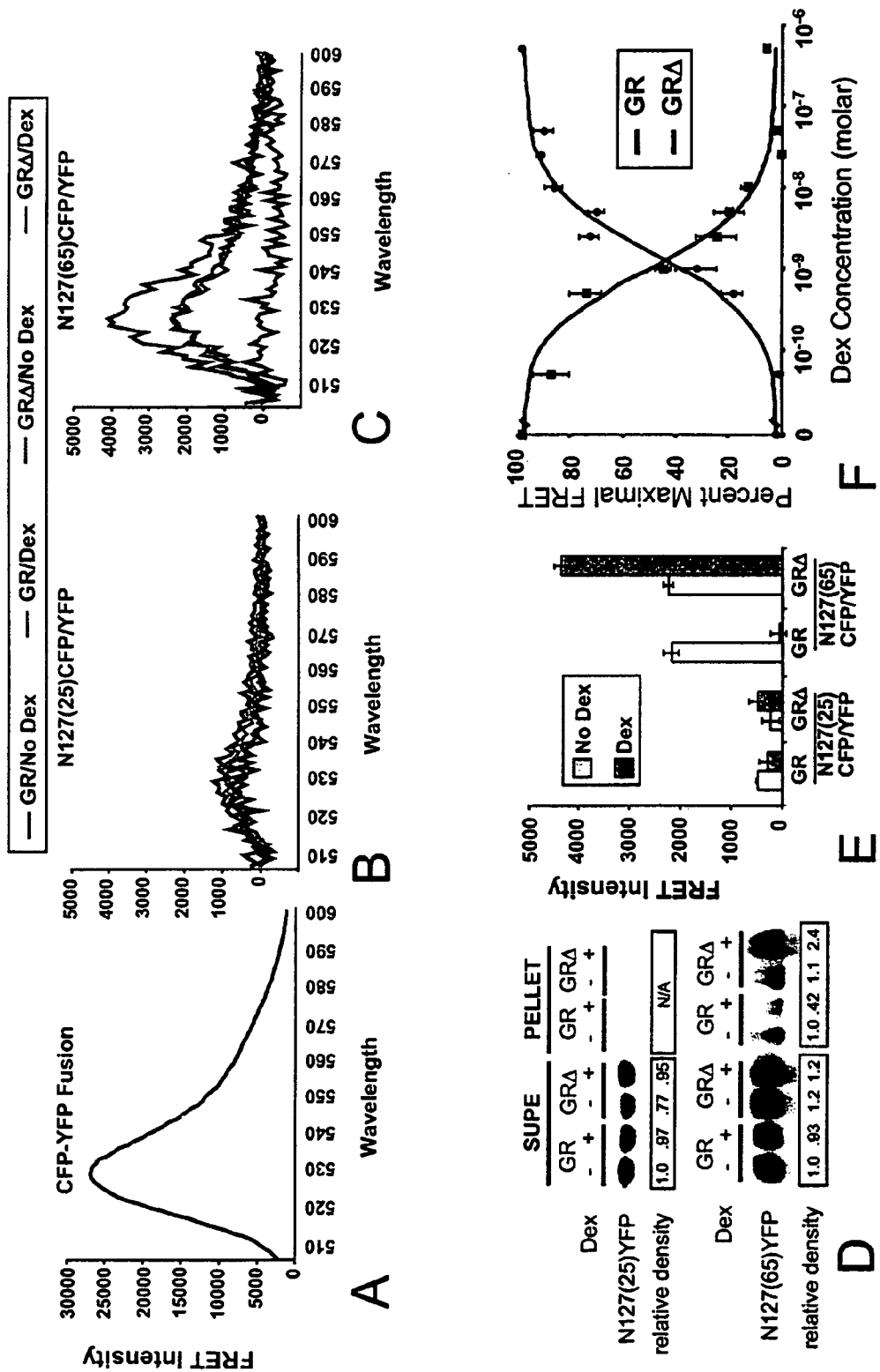
FIG. 2A illustrates detection of protein aggregation in cell monolayers using a fluorescence plate reader. Emission peaks with maxima near 527 nm (YFP emission maximum) indicate FRET; cells are expressing the YFP-CFP fusion.
FIG. 2B illustrates detection of polyglutamine protein aggregation in cell monolayers using a fluorescence plate reader. Emission peaks with maxima near 527 nm (YFP emission maximum) indicate FRET; cells are expressing ARN127 (25)CFP/YFP plus GR or GRΔ.
FIG. 2C illustrates detection of polyglutamine protein aggregation in cell monolayers using a fluorescence plate reader. Emission peaks with maxima near 527 nm (YFP emission maximum) indicate FRET; cells are expressing ARN127 (65)CFP/YFP plus GR or GRΔ in the absence of dex (blue and green curves), which were diminished by activated GR (pink), and increased by activated GRΔ (red). Note the scale differences on the Y axes.
FIG. 2D is a western blot of HEK293 cells transfected with ARN127(25)YFP or ARN127(65)YFP along with GR or GRΔ and immunoblotted with anti-AR antibody.
FIG. 2E is analysis FRET intensity of HEK293 cells transfected with ARN127(25)YFP or ARN127(65)YFP along with GR or GRΔ using excitation/emission windows on the FPR quantitatively reflect results from the emission scans. Error bars represent S.E.M.
FIG. 2F is a graph on percent maximal FRET as a function of dex concentration; $K_d$ for dex on GR and GRΔ is accurately re-derived via the FRET-based assay of aggregation. Curves were plotted as fractional signals with minimum signal arbitrarily set to zero and maximum set to 100.

To monitor polyglutamine protein aggregation based on FRET in transfected cell monolayers, an assay system was created using a monochrometer-based fluorescence plate reader (FPR). The cells HEK293 were used for their ease of transfection, high protein expression levels, and ability to induce a high degree of nuclear aggregation. Emission scans were performed using excitation at either 435 nm or 485 nm, and controls of CFP and YFP alone to calculate CFP bleedthrough into the YFP spectrum, and crossover activation of YFP by 435 nm excitation. These scans detected a robust FRET signal from cells expressing a positive control YFP-CFP fusion protein (FIG. 2A). Co-expression of individual CFP and YFP proteins produced no FRET, despite their colocalization as assayed by fluorescence microscopy (data not shown).

To characterize the system, changes were monitored in polyglutamine protein aggregation following dexamethasone (dex) activation of co-expressed GRor GRΔ, as described previously: when cultured with 100 mM dex, GR reduces AR and htt aggregation, whereas GRΔ increases nuclear aggregate formation and cell toxicity (Diamond et al., (2000) Proc Natl Acad Sci 97, 657-661; Welch and Diamond (2001) Hum Mol Genet 10, 3063-3074) (FIG. 1B). Highly specific and reproducible correlation between FRET signal and polyglutamine protein aggregation was observed. Emission scans on the FPR demonstrated a small FRET signal for ARN127 (25)CFP/YFP that was not significantly modulated by dex (FIG. 2B). By contrast, ARN127(65)CFP/YFP produced relatively strong FRET signals that were modulated as expected upon activation of GR (to prevent aggregation) or GRΔ (to increase aggregation) (FIG. 2C). These signals were approximately 10-20% of the signal from the YFP-CFP fusion.

The intensity of the FRET signal correlated well with measures of aggregate formation made by direct observation with fluorescence microscopy (data not shown), and by detergent fractionation. HEK293 cells were transfected with ARN127 (25)YFP or ARN127(65)YFP along with GR or GRΔ. After culture for 48 hours with or without 100 nM dex, cells were lysed in 1% TRITON®/PBS. Following centrifugation at 15,000×g, proportional amounts of SDS-denatured supernatant (SUPE) and pellet (PELLET) fractions were resolved by SDS-PAGE, and immunoblotted with anti-AR antibody. Band intensities were determined by densitometry. As shown in FIG. 2D, AR127(25)YFP did not produce significant amounts of detergent-insoluble material. AR127(65)YFP expression resulted in significant amounts of detergent-insoluble material that was decreased by GR and increased by GRΔ following addition of dex.

Example 3

Development of a High-Throughput Fret-Based Assay of Protein Aggregation

To create a high-throughput system, the two emission scans were replaced with three individual measurements using the following excitation/emission (ex/em) windows: CFP (435 nm ex/485 nm em), YFP (485 nm ex/530 nm em) and FRET (435 nm ex/530 nm em). This provided a quantitative measure of polyglutamine protein aggregation with no loss of fidelity (FIG. 2E). Dose-response titrations of dex using either GR (to suppress aggregation) or GRΔ (to increase aggregation) demonstrated the accuracy of this system, allowing re-derivation of the known $K_d$ of dex for GR and GRΔ (about 1 nM) using FRET as a readout (FIG. 2F). Thus, this detection method allows rapid and quantitative analysis of polyglutamine protein aggregation in a 96-well format.

The suitability of this system for high-throughput screening was confirmed by calculating the Z value to be 0.67 according to the formula: $1-(3\sigma_x+3\sigma_y)/|\mu_x-\mu_y|$, where $\sigma_x$ and $\sigma_y$ represent the standard deviation of positive and negative signals, respectively, and $\mu_x$ and $\mu_y$ represent the average value of the positive and negative signals, respectively (Zhang et al., (2000) J Comb Chem 2, 258-265). This number reflects the ability of a screen to distinguish two distinct signals, taking into consideration the mean value and standard deviation of each (in this case aggregated vs. non-aggregated polyglutamine protein); values>0.5 represent a highly robust system. The lower limit of detection of inhibition of protein aggregation was estimated to be about 10%.

Example 4

Limited Chemical Screen of Inhibitors of Polyglutamine Aggregation Identifies Y-27632 as a Protein Aggregation Regulator A number of well-characterized biologically active small molecules were tested, chosen on the basis of potential effects on polyglutamine protein aggregation and cell signaling. HEK 293 cells were transfected and re-plated in 96-well plates. Test wells were transfected with ARN127(65)CFP/YFP and GRΔ. Cells were cultured with 100 nM dex, which, in the context of GRΔ, produces predominantly nuclear aggregation. Test compounds were added to the culture medium in quadruplicate wells at the time of replating, and FRET measurements were taken after 48 hours. Compounds were screened at concentrations that were, where possible, approximately 2.5-, 5- and 10-fold over the reported $K_1$ or $EC_{50}$ for each.

Figure 3:
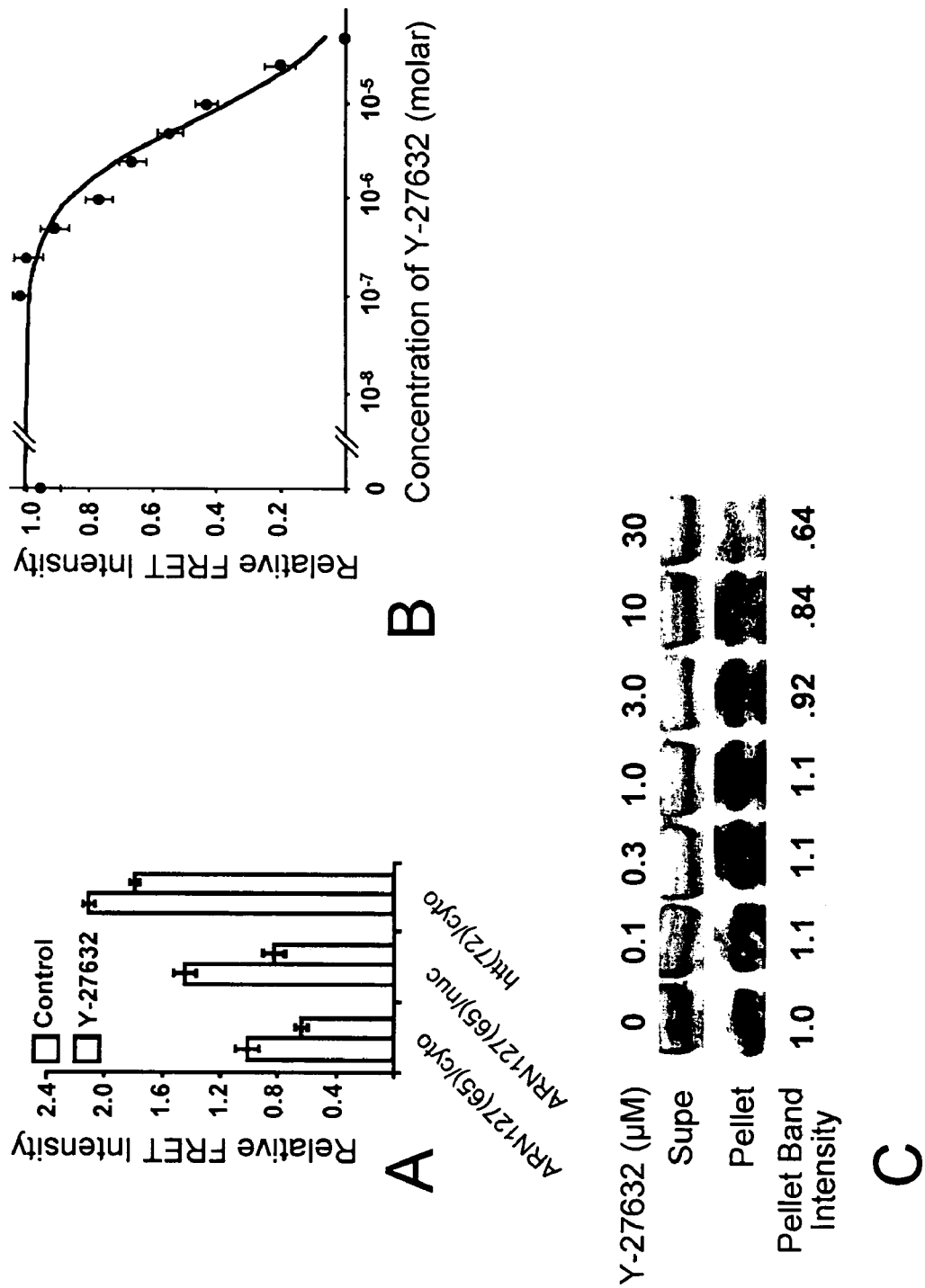
FIG. 3A illustrates that Y-27632 inhibits polyglutamine protein aggregation. FRET Intensity of ARN127(65)CFP/YFP in the absence of co-expressed GRΔ is set arbitrarily to 1. "nuc" and "cyto" refer to the predominant location of inclusions in each condition (nuclear vs. cytoplasmic).
FIG. 3B is a dose response analysis of Y-27632 inhibited aggregation; fractional FRET signals were plotted with minimum signal arbitrarily set to zero and maximum set to 100.
FIG. 3C is a western blot of HEK293 cells transfected with ARN127(65)YFP grown in the presence of increasing concentrations of Y-27632 followed by detergent fractionation, confirming the effect of Y-27632 on ARN127(65)YFP aggregation.

One compound, Y-27632, decreased FRET by 40%, without concomitant loss of CFP or YFP signal (FIG. 3A). The structure of Y-27632 is shown below.

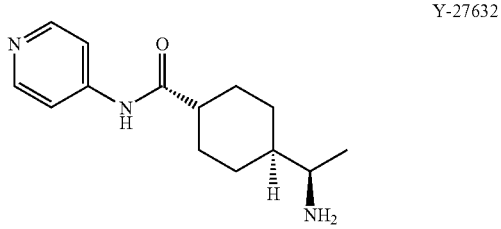

Y-27632

Y-27632 is a well-characterized inhibitor of the Rho-activated serine/threonine kinase, p160ROCK (Ishizaki et al., (2000) Mol Pharmacol 57, 976-983; Narumiya et al., (2000) Methods Enzymol 325, 273-284). A dose-response analysis demonstrated an $EC_{50}$ of approximately 5 µM for the effect of Y-27632 on polyglutamine aggregation (FIG. 3B). This is consistent with the $EC_{50}$ of Y-27632 in modulation of stress-fiber formation via inhibition of p160ROCK (Ishizaki et al., (2000) Mol Pharmacol 57, 976-983). Direct visualization (data not shown), and detergent fractionation confirmed the FPR findings (FIG. 3C). Y-27632 also inhibited aggregation of htt exon 1-CFP and -YFP fusions containing 72 repeats (htt(72)CFP/YFP) (FIG. 3A), demonstrating that its effects were not limited to a single polyglutamine protein.

Example 5

Primary High-Throughput Screen of Three Libraries

The high throughput AR based FRET screen was used to screen three libraries for candidate compounds that have potential as protein aggregation regulators. The Annotated Compound Library (ACL) (obtained from Brent Stockwell, Ph.D., Whitehead Institute) consisted of a collection of 2600 biologically active small molecules. A library of ≈350 kinase inhibitors was obtained from Kevan Shokat, Ph.D., UCSF. Finally, the NINDS collection of ≈1400 FDA-approved compounds was also screened.

Daughter plates were created in duplicate from the 384-well microtiter plates that contained the compounds at a single concentration, e.g., 80 µg/ml. Compounds were aliquoted in 96-well plates (Costar™ 3603) at a concentration of 4 µg/ml, at which most of the compounds are active, but are not toxic to the cells. To screen the library, HEK293 cells stably expressing RFP were plated in 10 cm plates to obtain ~80% confluency on the day of transfection. Each plate was transfected with 2 µg of ARN127(65)CFP/YFP each, and 0.7 µg p6RGRΔ using 50 µL Plus Reagent™ and 76 µL Lipofectamine™ according to manufacturer's protocol (Invitrogen). After 3 hours, complete medium was added and the plates were incubated further for 3 hours. Next, after adding 100 nM dex, the cells were counted and plated at a density of 70,000 cells/well in duplicate 96-well daughter plates containing single aliquots of compounds from the library. The cells were then cultured for ~48 hours to allow aggregate formation. After fixing the cells FRET signal was measured using a SAFIRE Fluorescence Plate Reader (Tecan, Inc.) according to methods described above. Several internal controls were used to standardize each experiment. Mock transfected cells were used to control for background autofluorescence and light scattering by mammalian cells. To control for CFP bleedthrough and crossover excitation of YFP, additional wells contained cells expressing ARN127(25)CFP or ARN127(25)YFP alone. RFP was measured to control for non-specific effects on steady-state protein levels. ARN127(25)CFP/YFP expression served as a reference point for background FRET levels without aggregation (a theoretical maximum effect on aggregation inhibition). FRET measurements for each experiment were thus scaled between 100% (cells with no drug treatment) and 0% (FRET levels from unexpanded protein). Last, each plate also contained wells treated with Y-27632 (50 µM) as a positive control.

In the primary screen of these libraries, most compounds had negligible effects on polyglutamine aggregation (0-30% reduction). In contrast a small number of compounds showed more robust effects of >50% reduction in aggregation. Table 2 includes data from the primary screen of a selected set of compounds from the ACL that inhibit polyglutamine aggregation.

TABLE 2

Selected ACL compounds exhibiting >60% inhibition of aggregation in primary high throughput screen.

| # | NAME | DESCRIPTION | % Inhibition |
|---|------|-------------|--------------|
| 1 | 2,4-Dichlorobenzylamine | None | 85% |
| 2 | Cytosine beta-D-arabinofuranoside Hydrochloride | Selective inhibitor of DNA synthesis; does not inhibit RNA synthesis. | 81% |
| 3 | N-(P-Tosyl)-L-Glutamine Isopropyl Ester | None | 80.6% |
| 4 | Sulfadiaine Free Acid | Antibacterial | 80% |
| 5 | N-6-Aminohexyl-1-Naphthalenesulfonamide | Calmodulin antagonist; inhibits Ca2/calmodulin activated phosphodiesterase and myosin light chain kinase | 79.7% |
| 6 | Azathioprine | Purine analog; immunosuppressive | 74.5% |
| 7 | L-Canavanine Free Base | selective inhibitor of inducible nitric oxide synthase (iNOS) | 73% |
| 8 | Allopurinol riboside | Anti-leishmanial agent | 71.8% |
| 9 | 8-Bromoguanosine 3',5'-cyclic monophosphate sodium salt | cell-permeable cGMP analog | 71% |
| 10 | Cefazolin sodium | Antimicrodial agent/antibiotic, used in coronary artery bypass graft surgery among other things | 70% |
| 11 | Methyl 3-O-(2-Acetamido-2-Deoxy-B-D-Glucopyranosyl)-B-D-Galactopyranoside | Substrate for beta-6-GlcNAc-transferase | 70% |
| 12 | Arphamenine B Hemisulfate Salt: Hydrate | Microbial source Inhibitor of aminopeptidase B | 69.7% |
| 13 | 4-Androsten-4-ol-3,17-dione 4-methyl ether | An aromatase inhibitor affecting estrogen-dependent processes. | 65.3% |
| 14 | A-77636 hydrochloride | Potent, orally active D1 dopamine receptor agonist | 64% |

Example 6

Secondary Screen of Selected Compounds

Selected candidate compounds from the primary screen of all three libraries were assayed again in a secondary screen using the AR FRET assay. Results are presented in Table 3 below.

TABLE 3

Compounds from three libraries exhibitinginhibition of aggregation in primary high throughput screen and secondary screen.

| Compound | Structure | IUPAC Name | Mechanistic Effects | Max % Inhibition |
|----------|-----------|------------|---------------------|------------------|
| Ac-YVAD-cmk | 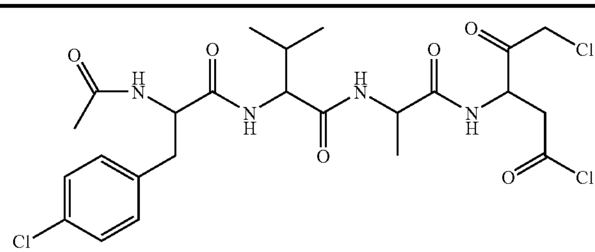 | N-Acetyl-Tyr-Val-Ala-Asp-chloromethylketone | Caspase 1 inhibitor | 29% |
| Piceatannol | 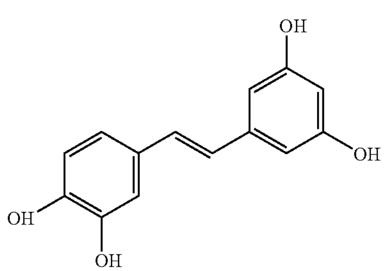 | 3,3'4,5'-Tetrahydroxy-Trans-stilbene | Syk Protein Tyrosine kinase inhibitor | 23% |
| Compound 3 | 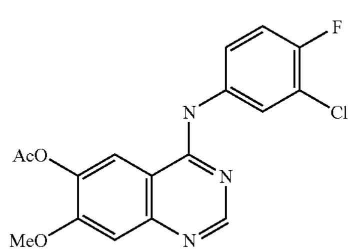 | Acetic acid 4-(3-chloro-4-fluoro-phenylamino)-7-methoxy-quinazolin-6-yl ester | EGFR Tyrosine kinase inhibitor | 30% |

TABLE 3-continued

Compounds from three libraries exhibiting inhibition of aggregation in primary high throughput screen and secondary screen.

| Compound | Structure | IUPAC Name | Mechanistic Effects | Max % Inhibition |
| --- | --- | --- | --- | --- |
| Compound 4 | 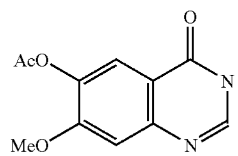 | Acetic acid 7-methoxy-4-oxo-3,4-dihydro-quinazolin-6-yl ester | EGFR Tyrosine kinase inhibitor | 28% |
| Iressa | 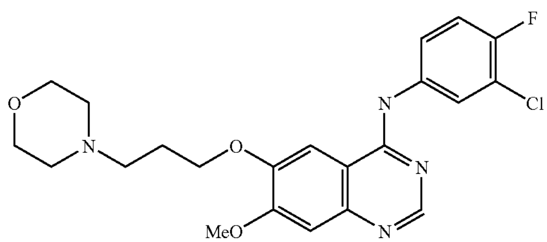 | (3-Chloro-4-fluoro-phenyl)-[7-methoxy-6-(3-morpholin-4-yl-propoxy)-quinazolin-4-yl]-amine | EGFR Tyrosine kinase inhibitor | 27% |
| Carbachol | 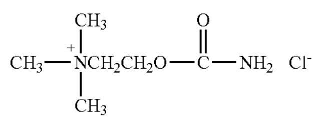 | (2-hydroxyethyl) trimethylammonium chloride carbamate | Muscarinic acetylcholine receptor agonist | 20% |
| Chloro-thiazide | 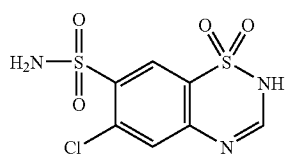 | 6-Chloro-2H-1,2,4-benzothiadiazine-7-sulfonamide 1,1-dioxide | | 19% |
| Betahistine hydro-chloride | 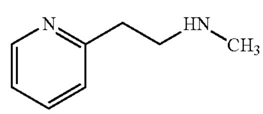 | N-methyl-N-(2-pyridin-2-ylethyl)amine dihydrochloride | Structural analogue of histamine. Upregulates histamine turnover and release by blocking H3 receptor | 19% |
| Molsido-mine | 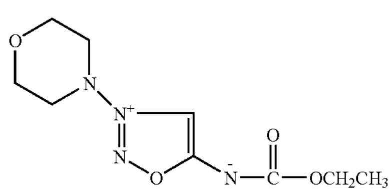 | N-(Ethoxycarbonyl)-3-(4-morpholino)sydnone imine | Nitric oxide donor | 20% |
| 1S,9R-beta hydrastine | 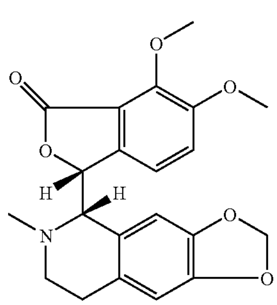 | 1S,9R-(+)-beta hydrastine | Competitive, mammalian GABA-A receptor antagonist | 18% |

TABLE 3-continued

Compounds from three libraries exhibiting inhibition of aggregation in primary high throughput screen and secondary screen.

| Compound | Structure | IUPAC Name | Mechanistic Effects | Max % Inhibition |
|---|---|---|---|---|
| Naringenin | 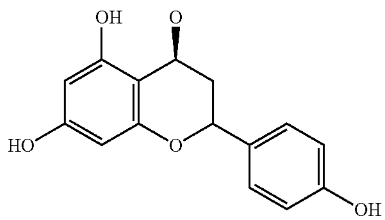 | (±)-2,3-Dihydro-5,7-dihydroxy-2-(4-hydroxyphenyl)-4H-1-benzopyran-4-one | | 19% |
| Fosfosal | 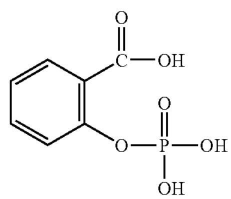 | 2-phosphonooxybenzoic acid | | 23% |
| Diltiazem HCl | 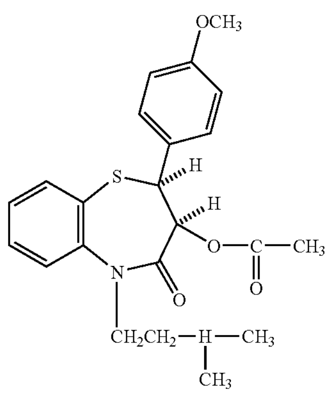 | (2S,3S)-(+)-cis-3-Acetoxy-5-(2-dimethylaminoethyl)-2,3-dihydro-2-(4-methoxyphenyl)-1,5-benzothiazepin-4(5H)-one hydrochloride | Ca channel blocker | 22% |
| Nadolol | 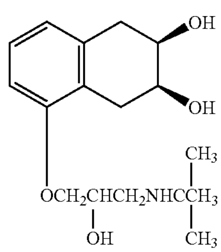 | | beta-adrenergic blocker | 19% |
| Spermidine HCl | 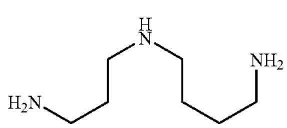 | N,N-bis(4-aminobutyl)amine | ornithine decarboxylase inhibitor | 19% |
| Diffractic acid | 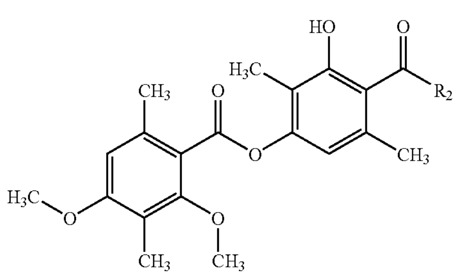 | 4-[(2,4-dimethoxy-3,6-dimethylbenzoyl)-oxy]-2-hydroxy-3,6-dimethylbenzoic acid | | 20% |

TABLE 3-continued

Compounds from three libraries exhibiting inhibition of aggregation in primary high throughput screen and secondary screen.

| Compound | Structure | IUPAC Name | Mechanistic Effects | Max % Inhibition |
|---|---|---|---|---|
| Alaproclate | [structure] | DL-alanine,2,4-chlorophenyl-1,1-dimethylethyl ester | Selective serotonin reuptake inhibitor (SSRI) | 17% |
| Leucodin | [structure] | (3S,9aR,9bS)-3,6,9-trimethyl-3,3a,4,5,9a,9b-hexahydroazuleno-[4,5-b]furan-2,7-dione | | 23% |
| Arachidonic acid | $CH_3(CH_2)_3CH_2(CH=CHCH_2)_4CH_2CH_2-C(=O)-OH$ | cis,cis,cis,cis-5,8,11,14-Eicosatetraenoic aci | prostaglandin & leucotriene precursor, stimulates NO biosynthesis | 19% |
| Minaprine HCl | [structure] | N-(4-Methyl-6-phenyl-3-pyridazinyl)-4-morpholineethanamin | Weak acetylcholinesterase inhibitor | 18% |

Selected compounds were assayed for inhibition of htt aggregation using the htt FRET assay described herein. The results are shown in Table 4 below.

TABLE 4

Compounds exhibit aggreagation of both AR aggregation and htt aggregation.

| Compound | Max % Inh. in Htt |
|---|---|
| Ac-YVAD-cmk | 32% |
| Piceatannol | 28% |
| Compound 3 | 21% |
| Compound 4 | 15% |
| Iressa | 20% |

These results demonstrate the power of this screening method to identify protein aggregation regulators across a large spectrum of compounds.

Example 7

Genetic Analysis of Pathways Implicated by Y-27632

Figure 5:
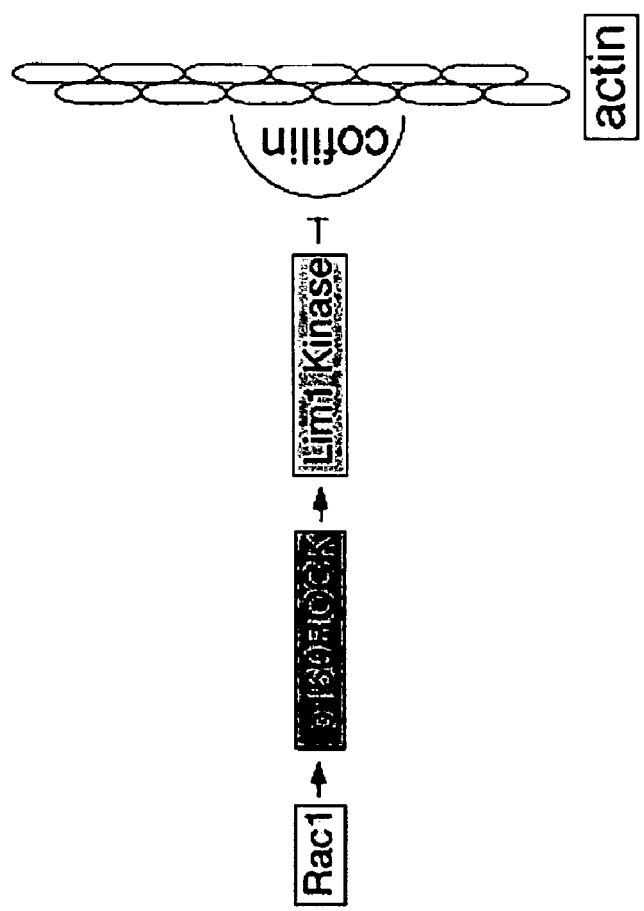
FIG. 5 is a diagram depicting the signaling cascade mediated by p160ROCK.

Y-27632 is a well-characterized inhibitor of the Rho-activated serine/threonine kinase, p160ROCK (Ishizaki, T., et al., 2000. Mol Pharmacol, 57(5): p. 976-83; Narumiya, S., et al 2000. Methods Enzymol 325:273-84; Uehata, M., et al. 1997-Nature 389:990-4). FIG. 5 illustrates the signaling cascade mediated by p160ROCK. Rac1 binds and activates p160ROCK, which phosphorylates and activates Lim-1 Kinase. Lim-1 Kinase phosphorylates and inactivates cofilin, an actin severing protein. Experiments were performed to investigate the role of this pathway in protein aggregation.

Figure 4:
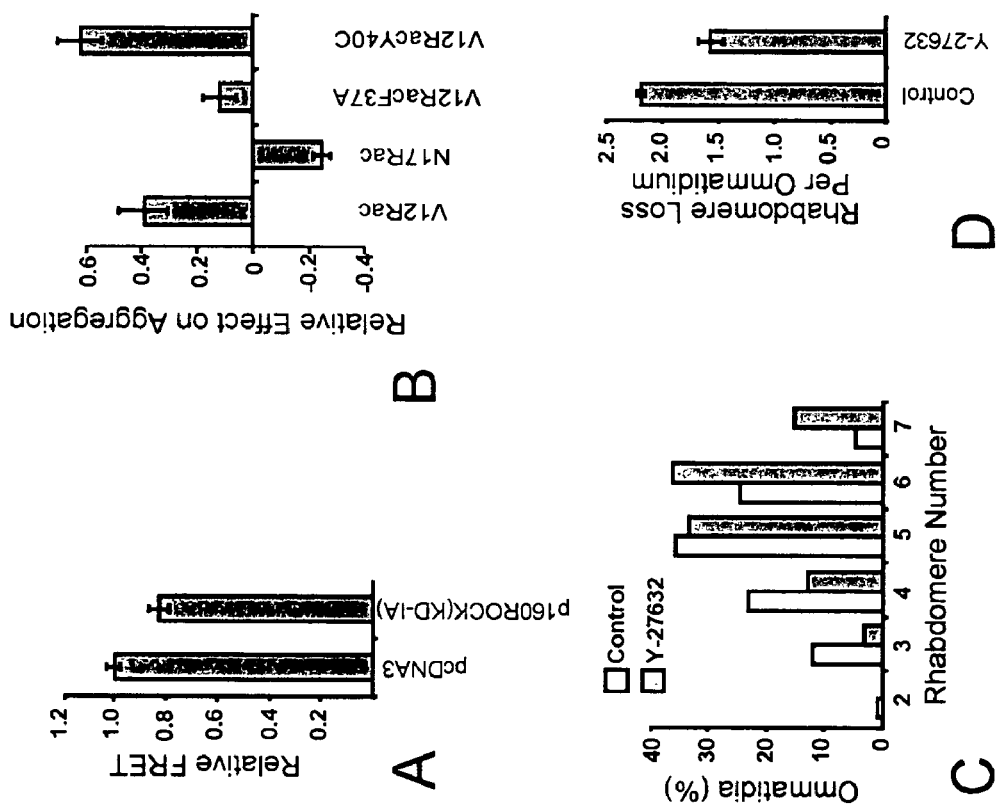
FIG. 4A is a histogram of FRET values with and without co-expression of p160ROCK(KD-IA), which reduced aggregation of AR127(65)CFP/YFP by about 20%.
FIG. 4B is a histogram of FRET values showing the effects on protein aggregation of dominant-positive V12Rac, dominant negative N17Rac; F37A V12Rac1 mutant; and Y40C V12Rac1 mutant.
FIG. 4C is a graph on the number of rhabdomeres per ommatidium in a *Drosophila* model of htt exon 1 toxicity; flies were treated with 25 μM Y-27632 in food.
FIG. 4D is a histogram of the average number of rhabdomeres/ommatidium per fly after treatment with Y-27632.

A dose-response analysis of Y-27632 demonstrated an $EC_{50}$ of approximately 5 µM for the effect of Y-27632 on polyglutamine aggregation; the result are shown in FIG. 3B. This is consistent with the $EC_{50}$ of Y-27632 in modulation of stress-fiber formation via inhibition of p160ROCK. The effect of a dominant-negative mutant, p160ROCK(KD-IA), on polyglutamine protein aggregation was assayed. The results are shown in FIG. 4A. Compared to empty expression vector, p160ROCK(KD-IA) decreased ARN127(65)CFP/YFP aggregation by about 20% (p<0.0001 by ANOVA). These results are consistent with the pharmacologic effects of Y-27632, and implicate p160ROCK in the cellular control of polyglutamine aggregation.

p160ROCK is best known as an effector of RhoA, but can also be controlled by other rho-GTPases, including Rac, to regulate cytoskeletal dynamics (Hirose et al., (1998). J Cell Biol 141, 1625-1636; Ishizaki et al., (1997). FEBS Lett 404, 118-124). To determine which GTPase might exert an effect on polyglutamine protein aggregation, constitutively active or dominant negative mutants of RhoA, Rac1, and Cdc42 were co-expressed with ARN127(65)CFP/YFP, and compared their effects to empty vector (pcDNA3). The results are shown in FIG. 4B. Dominant positive and negative RhoA and Cdc42 mutants each increased polyglutamine aggregation to varying degrees (data not shown). On the other hand, dominant negative N17Rac 1 suppressed aggregation about 20%, while its constitutively active counterpart, V12Rac1, increased polyglutamine aggregation about 40%. These experiments implicated the rho-GTPase family, and Rac1 in particular, as potential regulators of polyglutamine aggregation.

The role of Rac1 in this process was investigated by comparing two dominant-positive V12Rac1 mutants containing additional single amino acid substitutions in their effector loop domains. F37A selectively interferes with Rac1's interaction with p160ROCK, blocking regulation of lamellipodia formation while leaving intact its regulation of the JNK pathway. In contrast, Y40C has no effect on p160ROCK interaction, but blocks JNK activation (Lamarche et al., (1996). Cell 87, 519-529). The F37A mutation in V12Rac1 diminished its up-regulation of aggregation, whereas the Y40C mutation had no effect (FIG. 4B). Thus, Rac1 interaction with p160ROCK is crucial to its regulation of polyglutamine aggregation. Without wishing to be bound by theory, this suggests that Y-27632 functions via inhibition of p160ROCK, providing further evidence of the role of regulation of the cytoskeleton in the control of polyglutamine protein aggregation.

Of possible downstream targets of p160ROCK, expression of Lim-1 kinase increased polyglutamine aggregation significantly. Consistent with this result, expression of a non-phosphorylatable form of cofilin (S3A) potently reduced polyglutamine aggregation, whereas the wild-type form had only minimal effects (data not shown). Finally, the role of F-actin in preventing polyglutamine aggregation was investigated by treating cells with two agents that prevent actin depolymerization: phalloidin and jasplakinolide. The data is presented in Table 5 below. Both compounds reduced aggregation.

TABLE 5

Two agents that prevent actin depolymenrizastion inhibit protein aggreation.

| Compound | Structure | Mechanistic Effects | Max % Inhibition |
|---|---|---|---|
| Phalloidin | 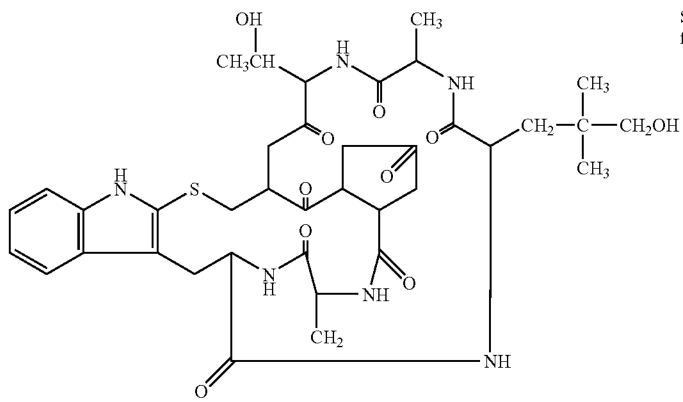 | Stabilizes actin filaments | 35% |
| Jasplakinolide | 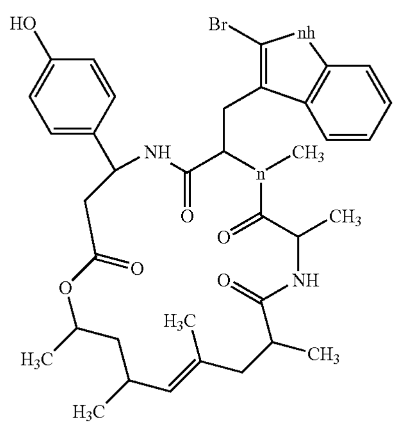 | Stabilizes actin filaments and enhances actin polymerization | 30% |

Slingshot (SSH-1) phosphatase counteracts the effects of Lim-1 kinase on cofilin. The effects of SSH-1 phosphatase on protein aggregation were investigated. HEK293 cells were co-transfected with ARN127(65)CFP/YFP, and the effects of wild-type SSH-1, or phosphatase-dead SSH-1 expression plasmid on Kim1 kinase protein aggregation were determined. High levels of SSH-1 expression increased polyglutamine aggregation, regardless of phosphatase activity. Intermediate levels of wt SSH-1 strongly reduced aggregation induced by Lim-1 Kinase, whereas phosphatase-dead SSH-1 did not reduce aggregation (data not shown).

These results identified components of the p160ROCK signaling pathway as playing a role in protein aggregation; a signaling pathway involved in actin regulation plays a role in protein aggregation can serve as drug targets.

Example 8

Analysis of Y-27632 in a *Drosophila* Model of Neurodegeneration

The therapeutic effect of Y-27632 in a *Drosophila* model of polyglutamine neurodegenerative disease was tested. Following eclosion, adult flies expressing the transgene were grown for seven days in the presence or absence of 25 µM Y-27632 in their food and rhabdomeres were counted at seven days. The results are shown in FIG. 4C and FIG. 4D. Drug treatment slowed the loss of photoreceptor neurons, as revealed by an increase in the average number of rhabdomeres per ommatidium, preventing 29% of the rhabdomere loss induced by polyglutamine protein over-expression (p<0.0003 by ANOVA). Thus, in addition to reducing polyglutamine aggregation in mammalian cells, Y-27632 is neuroprotective in this *Drosophila* model of polyglutamine protein toxicity.

Example 9

Y-27632 is Neuroprotective in a Cell Model of Full Length AR Cytopathology

Figure 6:
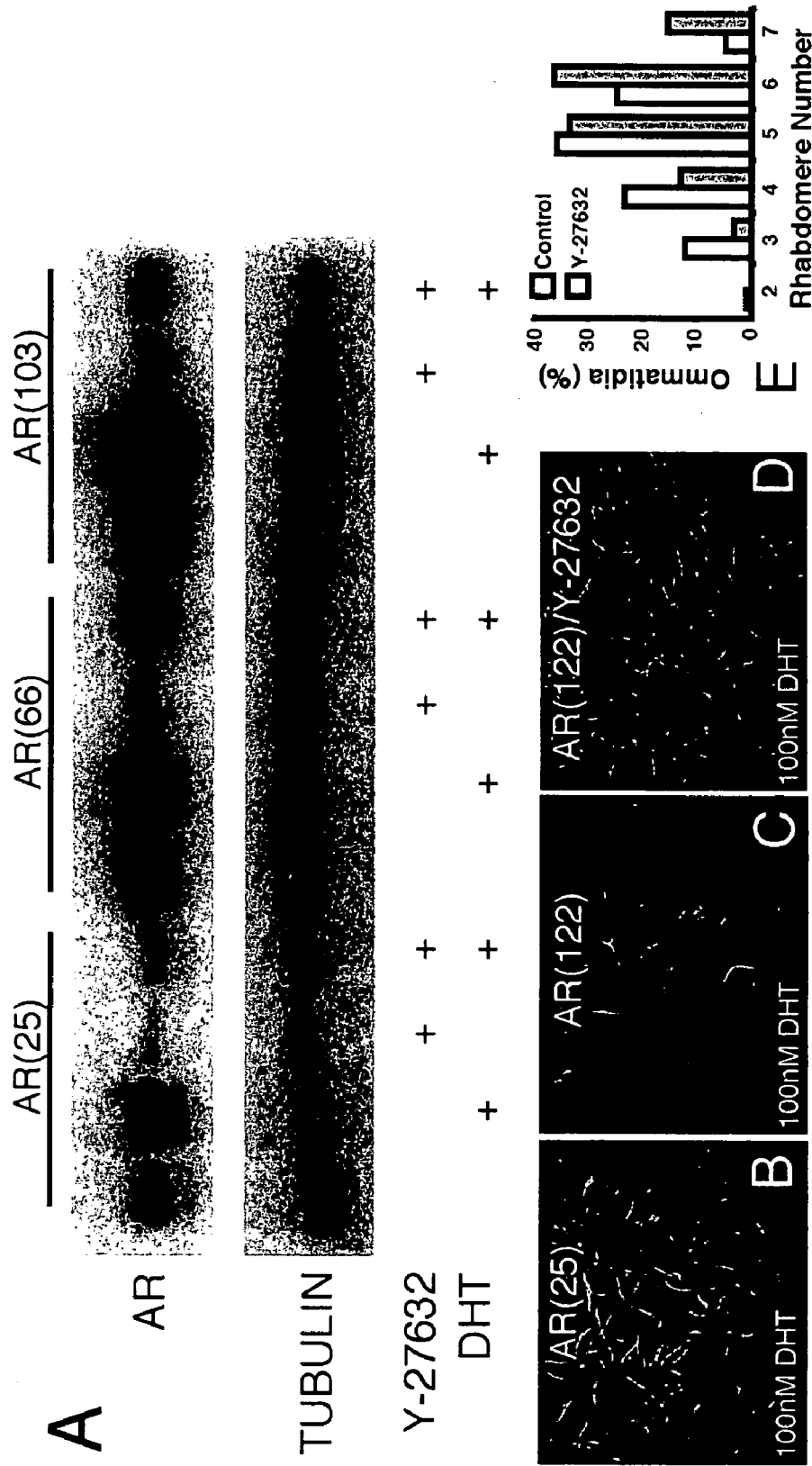
FIG. 6A is a western blot of cell extracts of C17.2 cells expressing AR constructs, treated with or without DHT and Y-27632.
FIG. 6B shows AR(25)-C17.2 cells after 6 days of differentiation; surviving neurons are indicated by red labeling of neuron-specific tubulin.
FIG. 6C shows AR(122)-C17.2 cells after 6 days of differentiation.
FIG. 6D shows AR(122)-C17.2 cells after 6 days of differentiation and treatment with 50 μM Y-27632.
FIG. 6E is the same chart as FIG. 4C and is a graph on the number of rhabdomeres per ommatidium in a *Drosophila* model of htt exon 1 toxicity; flies were treated with 25 μM Y-27632 in food.

The effects of Y-27632 on full-length AR levels and polyglutamine toxicity in stable cells was examined. C17.2 neural cell lines that were stably expressing full-length HA-tagged forms of AR (25, 66, 103, or 122 glutamines, AR(25), AR(66), AR(103), or AR(122)) were cultured with or without 100 nM DHT or 50 µM Y-27632. Western blots were performed using AR or tubulin antibodies to examine the effects of Y-27642 on full-length AR levels. As shown in FIG. 6A, Y-27632 reduced the AR steady-state levels, without affecting promoter transcription efficiency (data not shown).

The effects of Y-27632 on polyglutamine toxicity was examined. As shown in FIG. 6B, after 6 days of differentiation, AR(25)-C17.2 cells demonstrate many surviving neurons (indicated by red labeling of neuron-specific tubulin). As shown in FIG. 6C, AR(122)-C17.2 cells have many fewer neurons after differentiation. As shown in FIG. 6D, treatment with 50 µM Y-27632 increases by 100% the number of surviving AR(122)-C17.2 neurons, without affecting AR(25)-C17.2 cells (data not shown).

These results demonstrated that compounds identified by the FRET based protein aggregation HTS also affect protein aggregation in a cell model of protein aggregation.

Example 10

Y-27632 Bioavailability in Mice

Figure 7:
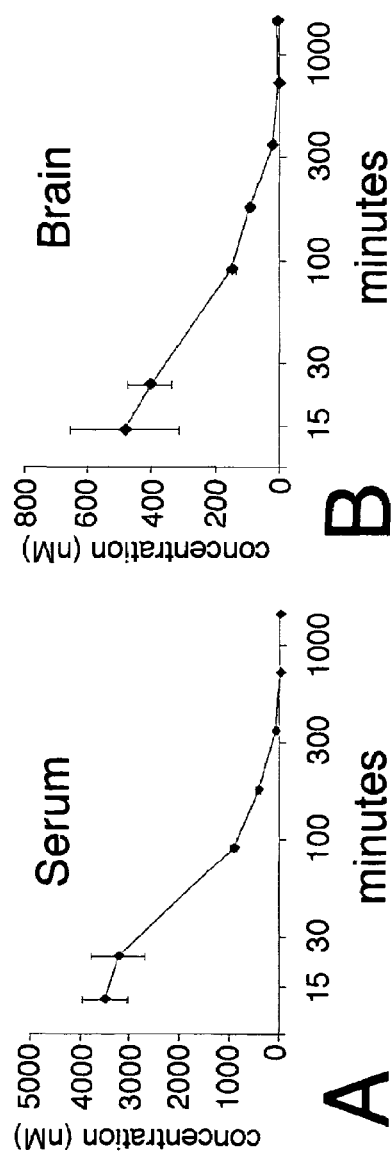
FIG. 7A is a graph of the pharmacokinetics of Y-27632 in serum of mice treated with a single dose of the drug. Values represent the average from two mice; error bars represent the range.
FIG. 7B is a graph of the pharmacokinetics of Y-27632 in brain of mice treated with a single dose of the drug. Values represent the average from two mice; error bars represent the range.

Experiments were performed that demonstrated Y-27632 has excellent bioavailability. Wild-type C57B6 mice were treated with a single 10 mg/kg dose of Y-27632 by IP injection. Pairs of animals were sacrificed at various time points and serum and brain samples were obtained for LC-MS analysis of Y-27632 levels. As shown in FIG. 7A, serum concentration vs. time indicates a spike to approximately 3.5 µM, followed by clearance with a t1/2≈60 min. The initial rapid fall in serum concentration is likely due to tissue redistribution. As shown in FIG. 7B, brain concentration vs. time indicates a lower overall level, with a peak at ≈500 nM. Values represent the average from two mice; error bars represent the range.

A rapid increase in serum levels was observed, which was followed by relatively rapid distribution into the brain. The serum:brain ratio was approximately 6:1, indicating relatively good penetration of the blood-brain barrier. Clearance rates from serum and brain were consistent with first-order kinetics, with a $t_{1/2}$ of approximately 60 minutes. These data suggested that systemic therapeutic effects observed in the literature might be achieved with peak serum levels of approximately 1 µM, although the relatively short half-life of Y-27632 suggests that these effects were achieved with much lower average serum levels.

Example 11

Testing Candidate Compounds in Mouse Models of Protein Aggregation Diseases

Candidate compounds for treatment of protein aggregation diseases were identified as described herein using the high throughput screen and further characterized using the secondary screens (e.g., AR FRET assay, htt FRET assay, cell model of full-length AR cytopathology, *Drosophila* model of neurodegeneration). Selected candidate compounds are further characterized using animal models, e.g., mouse models.

First, the pharmacodynamic properties of the candidate compounds are examined and an optimal dosing regimen is determined. Second, an optimal dose of a candidate compound is administered over several months to a full-length AR mouse line and AR protein intracellular misfolding is examined. Finally, tests are performed using a mouse model expressing a truncated polyglutamine protein, htt exon 1, to examine the efficacy of a candidate compound in improving the neurodegenerative phenotype. These experiments aid in determination of the therapeutic potential of candidate compounds. A candidate compound that demonstrate s efficacy in either mouse model is a potential therapy that could be developed further for tests in humans.

Two animal models are used in parallel to overcome the limitations of each in isolation. The AR112 (Chevalier-Larsen, E. S., et al. 2004 J Neurosci 24(20):4778-86) line has advantages for development of a therapy for SBMA: it uses a full-length form of the pathogenic AR protein; it has slowly progressive motor neuron dysfunction that more closely mimics human disease; and it selectively afflicts males. However, because the disease course is slow, and the phenotype relatively mild, it requires larger numbers of animals to achieve statistical significance for a given degree of benefit. Likewise, the time frame for analysis of a test therapy is relatively prolonged. R6/2 animals (Mangiarini, L., et al., 1996 Cell 87: 493-506; Davies, S. W., et al., 1997 Cell 90:537-48; Hockly, E., et al. 2003 Brain Res Bull 61:469-79) which express a truncated fragment (exon 1) of the htt protein, have a pan-neuronal phenotype that does not represent a true model of any single polyglutamine disease. However, their relatively rapid disease onset and progression, and a very predictable disease course, make them very useful to study the potential therapeutic benefit of candidate compounds.

1. Determine Optimal Dosing of Candidate Compounds in Mice

The maximum tolerated dose and bioavailability of candidate compounds are determined.

Cohorts of animals are treated with a range of doses (e.g., 10-300 mg/kg/day for Y-27632), both oral and intraperitoneal (IP). Five animals in each group are treated with administration either in drinking water or via IP injection. Animals are treated for one week, with daily weights, and monitoring of food and water intake. They are observed for signs of drug toxicity, including weight loss, poor grooming, poor movement, ataxia, or tremors. At the end of the observation period, and one hour after a final dose (in the case of IP injections), animals are sacrificed. Brain and serum samples are collected and subjected to HPLC and mass spectrometry (LC-MS) to determine drug levels. The LC-MS is performed in collaboration with the laboratory of Emil Lin, Ph.D. (UCSF). For some candidate compounds, e.g., Y-27632, the level of p160ROCK activity within the brain is determined by western blot of a phosphorylation target of p160ROCK (myosin light chain kinase) using phospho- and non-phospho-specific antibodies (Miyazaki, K., et al., 2002 J Biol Chem 277:725-34). Alternatively, p160ROCK activity is determined using kinase assays after precipitating p160ROCK from treated and untreated mouse brain (Uehata, M., et al. 1997 Nature 389: 990-4). These studies will indicate the brain levels achieved using specific doses of candidate compounds, e.g., Y-27632, ideally, e.g., 1-5 µM, the extent to which these doses inhibit p160ROCK, and the extent to which these levels are tolerated on a chronic basis in mice.

Alternatively, candidate compounds are delivered to mice directly into the intraventricular space using an osmotic pump system (e.g., Alzet, Cupertino, Calif.).

2. Testing Effects of Candidate Compounds on Ar Inclusion Formation, Aggregation, Steady-State Levels, and Neuropathology in AR112 Mice The effects of chronic administration of candidate compounds, e.g., Y-27632, on key aspects of protein misfolding and steady state in AR112 mice are determined. Cohorts of 30 mice each for the AR112 lines (male and female, wild-type and transgenic) are established. Utilizing the dosing regimen determined above, animals receive daily drug treatment, beginning at age 3 weeks (weaning), and continuing for three months. Nuclear inclusions are readily visible at 3-4 months; biochemical assays (slot blot and western analyses) are used to measure the detergent insolubility of AR protein in these animals.

At one month intervals, five treated and untreated animals from each cohort are sacrificed, and brain samples removed for histopathology and biochemical analyses. Histopathology consists of staining with the N-20 AR antibody, which recognizes 20 amino acids at the amino-terminus of AR. Brain sections are analyzed by fluorescence microscopy to determine whether treatment effects a change in nuclear inclusion size and frequency vs. control animals.

Biochemical studies consist of fractionation with non-ionic detergent. Brain homogenates are subjected to centrifugation at 15,000×g. Supernatant fractions are resolved directly by SDS-PAGE. The pellet fractions are divided into two aliquots: one is resuspended in SDS-sample buffer, followed by SDS-PAGE; the second is resuspended in fractionation buffer containing non-ionic detergent and loaded on a vacuum manifold (slot blot apparatus). The slot-blot samples are vacuum-filtered through a 0.45 µm nitrocellulose membrane. The membrane is subsequently blotted with N-20 antibody. Gels of SDS-soluble material (containing non-ionic detergent soluble vs. insoluble fractions) are subjected to western blot followed by band densitometry. Housekeeping proteins (e.g. GAPDH) are measured in parallel as loading controls. These measurements allow determination of the relative amount of detergent-soluble and insoluble AR, and allow semi-quantitative assessment of protein misfolding and aggregation.

Studies are then performed to investigate the effect of candidate compounds on disease progression, e.g., neurodegenerative phenotype, in the AR112 line.

3. Testing Effects of Candidate Compounds on Polyglutamine-Dependent Neuropathology in R6/2 Mice The effects of candidate compounds, e.g., Y-27632, on polyglutamine-dependent neuropathology in the R6/2 mouse model are examined.

The R6/2 line was created by driving expression of an htt exon-1 fragment from the htt promoter. While not a precise model of human HD, it serves as a model of "polyglutaminopathy," with widespread inclusion formation, and neuronal dysfunction. This line has been extraordinarily well-characterized as an experimental system. It has a relatively rapid and predictable disease course, meaning that relatively few animals and a relatively short time course are needed to determine whether a test intervention is effective. Animals show early evidence of neuronal inclusion formation (e.g., by several weeks of age), progressive weight loss, declining rotarod performance, tremors, seizures, and early death by approximately 15 weeks of age (Gutekunst, C. A., et al. 1999 Journal of Neuroscience 19:2522-34; Bolivar, V. J. et al. 2003 Behav Neurosci 117:1233-42; Chen, M., et al. 2000 Nat Med 6:797-801).

Wild-type females with ovaries transplanted from R6/2 animals (Jackson Labs) are used to breed R6/2 offspring. At the time of weaning (2-3 weeks) R6/2 littermate animals receive candidate compounds (dosing schedule determined as described herein) or vehicle control, to produce four cohorts each of 30 female animals. Males are excluded due to their severe weight loss. At 4 week intervals over the course of the study, groups of 5 animals are sacrificed for tissue analysis, including brain weight, histopathologic analysis to measure the relative amounts of inclusion formation, and detergent fractionation in 1% TRITON® X-100 to measure aggregation levels via biochemistry, in a manner similar to experiments done with AR112 mice. For immunohistochemical and biochemical studies, the EM48 antibody is used to identify htt inclusions in brain, and has been widely used to document the effects of various interventions on this process.

Behavioral analysis of R6/2 animals is performed using several tests. Four cohorts of animals are studied: gene negative controls with and without candidate compound treatment, and gene positive animals with and without candidate compound treatment. After genotyping, the investigations are carried out blinded to the genotype of the animals and treatment. The R6/2 neurologic phenotype is severe, and manifests with several easily measured signs: weight loss, abnormal home cage behavior (rearing, movement), decreasing rotarod performance, clasping, tremor, and handling-induced seizures. Other early learning and memory deficits have been described, but interpretation of these phenomena is difficult in the context of progressive disease, because they can only be assessed early, before sensory/motor deficits confound assessment of cognitive function. The following protocols are to determine the effectiveness of drug therapy.

Weight: R6/2 mice show progressive weight loss with disease. Animals are weighed twice weekly.

Rotarod: Animals are assessed every two weeks on an accelerating rotarod apparatus (Rotamex, Columbus Instruments). Four animals per session are placed on the rotarod, which is set to accelerate gradually from 10 to 40 rpm over 10 minutes. When animals fall off the rod, this trips a light beam that stops the timer. Each mouse is tested four times, with at least a 15 minute rest period between individual sessions. This multi-modal test, which is sensitive to weakness as well as discoordination, is highly quantifiable and reproducible. Although learning and memory play some role in test performance, the same test is used repetitively with reproducible results for a single animal.

Clasping: When suspended by the tail for several seconds, the R6/2 line shows a highly characteristic motor response consisting of an abnormal clasping of all four limbs, whereas a wild-type mouse spreads its limbs out. The anatomic source of this motor behavior is unknown (it may represent upper motor neuron dysfunction) however it has a defined onset within the R6/2 line and is thus a robust marker of disease. Animals shall be scored for this activity on a twice-weekly basis.

Tremor/Seizure: Tremors and handling-induced seizures are late-stage manifestations of disease due to CNS dysfunction and are relatively easy to note. Animals are scored for these behaviors on a twice-weekly basis.

Grip Strength: The R/2 animals show progressive loss of grip strength, and are tested using a grip strength meter (Columbus Instruments) one time per week.

All references, issued patents and patent applications cited within the body of the instant specification are hereby incorporated by reference in their entirety, for all purposes.

What is claimed is:

1. A method of modulating aggregation of a first protein in a cell, wherein the first protein aggregates in the cell and is selected from the group consisting of a polyglutamine protein, a tau protein, a synuclein, a superoxide dismutase, a PABPN1, an Aβ peptide, a serpin, a transthyretin, an ataxin, and a prion protein, the method comprising administering a sufficient amount of a protein aggregation regulator to the cell, wherein said protein aggregation regulator comprises a small molecule, such that aggregation of the first protein is modulated.

2. The method of claim 1, wherein said first protein comprises a polyglutamine protein.

3. The method of claim 2, wherein said first protein comprises an androgen receptor (AR) or an huntingtin protein (htt).

4. The method of claim 1, wherein said first protein is selected from the group consisting of a tau protein, a synuclein, a superoxide dismutase, a polyA binding protein nuclear 1 (PABPN1), an Aβ peptide, a serpin, a transthyretin, an ataxin, and a prion protein.

5. The method of claim 1, wherein said sufficient amount reduces aggregation of the first protein by at least 10% or at least 20% or at least 40%.

6. The method of claim 1, wherein said small molecule comprises Y-27632.

7. The method of claim 1, wherein said protein aggregation regulator modulates an activity of a second protein selected from the group consisting of a p160ROCK, a rho-GTPase, a RhoA, a Cdc42, a Rac1, a Lim-1 kinase, a cofilin, and a slingshot phosphatase.

8. The method of claim 7, wherein said protein aggregation regulator inhibits p160ROCK.

9. The method of claim 1, wherein said protein aggregation regulator comprises a caspase 1 inhibitor.

10. The method of claim 1, wherein said protein aggregation regulator comprises a kinase inhibitor.

11. The method of claim 1, wherein said protein aggregation regulator comprises Piceatannol, Acetic acid 4-(3-chloro-4-fluoro-phenylamino)-7-methoxy-quinazolin-6-yl ester, Acetic acid 7-methoxy-4-oxo-3,4-dihydro-quinazolin-6-yl ester, Iressa, Phalloidin, Jasplakinolide, Hydralazine HCl, Carbachol, Chlorothiazide, Betahistine hydrochloride, Molsidomine, 1S,9R-beta hydrastin, Naringenin, Fosfosal, Diltiazem HCl, Nadolol, Spermidine HCl, Diffractic acid, Alaproclate, Leucodin, Arachidonic acid, or Minaprine HCl.

12. The method claim 1, wherein said protein aggregation regulator modulates a target in a pathway, wherein said pathway is modulated by a compound comprising Piceatannol, Compound 3, Compound 4, Iressa, Phalloidin, Jasplakinolide, Hydralazine HCl, Carbachol, Chlorothiazide, Betahistine hydrochloride, Molsidomine, 1S,9R-beta hydrastin, Naringenin, Fosfosal, Diltiazem HCl, Nadolol, Spermidine HCl, Diffractic acid, Alaproclate, Leucodin, Arachidonic acid, or Minaprine HCl.

13. The method of claim 1, wherein said method comprises reducing aggregation of an androgen receptor in a HEK293 cell comprising administering a sufficient amount of Y-27632.

14. The method of claim 1, wherein said method is performed in vivo.

15. The method of claim 14, wherein said method is performed in mice or fruit flies.

16. The method of claim 14, further comprising monitoring aggregation of the first protein in the cell.

17. The method of claim 1, wherein said method is performed in situ.

18. The method of claim 17, further comprising monitoring aggregation of the first protein in the cell.

* * * * *